(12) United States Patent
Gei et al.

(10) Patent No.: US 12,011,602 B2
(45) Date of Patent: Jun. 18, 2024

(54) WIRELESS POWER FOR PESSARY DEVICE

(71) Applicant: Obstetric Solutions LLC

(72) Inventors: Alfredo F. Gei, Houston, TX (US); David Esteban Paniagua Gonzalez, Houston, TX (US); David Paniagua, Houston, TX (US)

(73) Assignee: Obstetric Solutions LLC, Houston, TX (US)

( * ) Notice: Subject to any disclaimer, the term of this patent is extended or adjusted under 35 U.S.C. 154(b) by 883 days.

(21) Appl. No.: 17/061,444

(22) Filed: Oct. 1, 2020

(65) Prior Publication Data

US 2021/0016098 A1 Jan. 21, 2021

Related U.S. Application Data

(63) Continuation-in-part of application No. 16/444,279, filed on Jun. 18, 2019, now Pat. No. 11,872,395.

(51) Int. Cl.
*A61N 1/372* (2006.01)
*A61B 5/00* (2006.01)
(Continued)

(52) U.S. Cl.
CPC .......... *A61N 1/37229* (2013.01); *A61F 2/005* (2013.01); *A61F 6/08* (2013.01); *A61N 1/3787* (2013.01)

(58) Field of Classification Search
CPC ... A61N 1/00; A61N 1/18; A61N 1/32; A61N 1/36; A61N 1/372;
(Continued)

(56) References Cited

U.S. PATENT DOCUMENTS

| 436,861 A | 9/1890 | Sherwood |
| 2,324,656 A * | 7/1943 | Cranston ................... A61F 6/08 128/837 |

(Continued)

FOREIGN PATENT DOCUMENTS

| DE | 10345282 B3 * | 4/2005 | ......... A61B 10/0012 |
| WO | WO-2011113934 A1 * | 9/2011 | .......... A61M 1/1037 |

(Continued)

OTHER PUBLICATIONS

Aran, T. et al. "Association between preterm labour and pelvic floor muscle function," J. Obstet.Gynaecol., vol. 38, Issue 8, 2018.
(Continued)

*Primary Examiner* — Michelle J Lee
(74) *Attorney, Agent, or Firm* — Norton Rose Fulbright US LLP

(57) ABSTRACT

A pessary for the prevention of preterm birth, and in particular two pathological conditions of pregnancy known as isthmico-cervical incontinence and cervical shortening, both of which are associated with increased risks for pregnancy loss and/or premature deliveries of babies. The pessary includes a sleeve supported within a ring by an annular member. The sleeve is intended to contact the cervix and maximize the length of the cervix while the annular member and ring contact the vagina. The pessary may be fabricated from a pliable medical-grade silicon, and the pessary may include one or more sensors to measure various patient parameters indicative of a premature cervical contraction. The sleeve may be wirelessly powered from a charging device, such as a pillow, a table-top device, or a pelvic belt.

12 Claims, 25 Drawing Sheets

(51) Int. Cl.
| | |
|---|---|
| *A61B 5/01* | (2006.01) |
| *A61B 5/11* | (2006.01) |
| *A61B 5/145* | (2006.01) |
| *A61F 2/00* | (2006.01) |
| *A61F 6/08* | (2006.01) |
| *A61K 31/57* | (2006.01) |
| *A61N 1/05* | (2006.01) |
| *A61N 1/36* | (2006.01) |
| *A61N 1/378* | (2006.01) |

(58) Field of Classification Search
CPC .... A61N 1/37211–37229; A61N 1/378; A61N 1/3787; A61F 2/00–005; A61F 6/00; A61F 6/06; A61F 6/12; A61B 5/00–0004; A61B 5/0011; A61B 5/0015; A61B 5/0024; A61B 5/0031; A61B 5/01; A61B 5/0215; A61B 5/02158; A61B 5/11; A61B 5/1107; A61B 5/145; A61K 31/56; A61K 31/57; A61K 31/573
See application file for complete search history.

(56) References Cited

U.S. PATENT DOCUMENTS

| | | | |
|---|---|---|---|
| 3,404,682 | A | 10/1968 | Waldron |
| 4,311,543 | A | 1/1982 | Strickman et al. |
| 4,711,235 | A | 12/1987 | Willis |
| 5,065,772 | A | 11/1991 | Cox, Jr. |
| 5,207,232 | A * | 5/1993 | Shihata ............ A61F 6/08 128/838 |
| 5,406,961 | A * | 4/1995 | Artal ............ A61B 5/1076 600/587 |
| 6,039,701 | A | 3/2000 | Sliwa et al. |
| 6,086,909 | A | 7/2000 | Harrison et al. |
| 8,408,212 | B2 | 4/2013 | O'Brien et al. |
| 8,573,221 | B2 | 11/2013 | Sakhel |
| 9,474,885 | B2 | 10/2016 | Cline et al. |
| 9,764,120 | B2 | 9/2017 | Cline et al. |
| 9,820,994 | B2 | 11/2017 | Campos Perez et al. |
| 10,874,432 | B2 * | 12/2020 | La Vean ............ A61B 17/425 |
| 2008/0121238 | A1 * | 5/2008 | Shihata ............ A61F 6/12 128/833 |
| 2008/0171950 | A1 * | 7/2008 | Franco ............ A61B 5/0538 604/66 |
| 2009/0082832 | A1 * | 3/2009 | Carbunaru ............ A61N 1/3787 607/59 |
| 2013/0053670 | A1 | 2/2013 | Aina-Mumuney et al. |
| 2014/0073879 | A1 * | 3/2014 | Cantor ............ A61B 5/435 600/304 |
| 2015/0265456 | A1 | 9/2015 | Booher, Sr. |
| 2017/0020529 | A1 | 1/2017 | Tsur et al. |
| 2019/0008674 | A1 | 1/2019 | Myers et al. |
| 2019/0160332 | A1 | 5/2019 | Beer et al. |
| 2020/0086110 | A1 | 3/2020 | Karsdon et al. |
| 2021/0177645 | A1 * | 6/2021 | Crafton ............ A61F 6/12 |

FOREIGN PATENT DOCUMENTS

| | | | |
|---|---|---|---|
| WO | WO-2016199115 A2 | 12/2016 | |
| WO | WO-2017152029 A1 | 9/2017 | |
| WO | WO-2018119052 A1 | 6/2018 | |
| WO | WO-2019084469 A1 * | 5/2019 | ........... A61B 5/0004 |
| WO | WO-2019226441 A1 | 11/2019 | |

OTHER PUBLICATIONS

Alfirevic, Z., et al., "Vaginal progesterone, cerclage or cervical pessary for preventing preterm birth in asymptomatic singleton pregnant women with a history of preterm birth and a sonographic short cervix," Ultrasound Obstet. Gynecol, Feb. 2013 (6 pages).

Berghella, V., et al., "Prevention of preterm birth with pessary in twins (PoPPT): a randomized controlled trial," Ultrasound Obstet Gynecol. May 2017 (2 pages).

Berghella, V., et al., "Twins with short cervix: hope ahead," BJOG: An International Journal of Obstetrics and Gynaecology, (1 page).

Biggio, J. et al., "Spontaneous Preterm Birth in Multiples," Clinical Obstetrics and Gynecology, vol. 58, No. 3, pp. 654-657 (14 pages).

Cabrera-Garcia, L., et al., "Evaluation of two treatment strategies for the prevention of preterm birth in women identified as a risk by ultrasound (PESAPRO Trial): study protocol for a randomized controlled trial," Trials: Study Protocol (10 pages).

Cannie, M., et al., "Arabin cervical pessary in women at high risk of preterm birth: a magnetic resonance imaging observational follow-up study," Ultrasound Obstet. Gynecol 2013 (8 pages).

Collins, A., et al., "A clinical opinion on how to manage the risk of preterm birth in twins based on literature review," The Journal of Maternal-Fetal & Neonatal Medicine, May 22, 2015. (7 pages).

Dharan, V., et al., "Alternative Treatment for a Short Cervix: The Cervical Pessary," Elsevier: Seminars in Perinatology, 2009 (5 pages).

DiTommaso, M., et al., "Arabin cervical pessary to prevent preterm birth in twin pregnancies with short cervix," Journal of Obstetrics and Gynaecology, 2016 (5 pages).

Dugoff, I., et al., Prevention of preterm birth with pessary in singletons (PoPPS): randomized controlled trial Ultrasound Obstet. Gynecol, 2018 (8 pages).

Folterman, C., "Cervical Pessary and Vaginal Progesterone in Twin Pregnancies with a Short Cervix," The American College of Obstetricians and Gynecologists, Aug. 2016 (2 pages).

Fox, N., et al., "Cervical Pessary and Vaginal Progesterone in Twin Pregnancies with a Short Cervix," Obstetrics & Gynecology, vol. 127, No. 4, Apr. 2016 (6 pages).

Fuchs, F., et al., "Multiple gestations and preterm birth," Seminars in Fetal & Neonatal Medicine, 2016 (8 pages).

Gilner, J., et al., "Management of Short Cervix during Pregnancy", American Journal of Perinatology, Review Prematurity Special Issue, vol. 33, No. 3, 2016 (8 pages).

Goya, M. et al., Cervical pessary in pregnant women with a short cervix (PECEP): an open-label randomised controlled trial, www.thelancet.com, vol. 379, May 12, 2012 (3 pages).

Goya, M. et al., Cervical pessary to prevent preterm birth in women with twin gestation and sonographic short cervix: a multicenter randomized controlled trial (PECEP-Twins), American Journal of Obstetrics & Gynecology, Feb. 2016 (8 pages).

H., A., et al., Cervical pessary for preventing preterm birth (Review), The Cochrane Collaboration, 2013, Issue 5, Art. No. CD007873 (29 pages).

Hermans, F., et al., Effectiveness of a cervical pessary for women who did not deliver 48 h after threatened preterm labor (Assessment of perinatal outcome after specific treatment in early labor: Apostel VI trial), BMC Pregnancy and Childbirth, 2016 (6 pages).

Hezelgrave, N., et al., "Rationale and design of SuppOrt: a multicentre randomised controlled trial to compare three treatments: cervical cerclage, cervical pessary and vaginal progesterone, for the prevention of preterm birth in women who develop a short cervix," BMG Pregnancy and Childbirth: 2016 (10 pages).

Houda, M., et al., "Cervical pessary in in pregnant women with a short cervix," www.thelancet.com, vol. 380, Sep. 8, 2012 (2 pages).

Hui, A., et al., "Cerclage Pessary for Preventing Preterm Birth in Women with a Singleton Pregnancy and a Short Cervix at 20 to 24 Weeks: A Randomized Controlled Trial," American Journal of Perinatology, vol. 30, No. 4, 2013 (6 pages).

Huras, H., et al., "Short cervix in twin pregnancies: current state of knowledge and the proposed scheme of treatment," Ginekologia Polska 2017, vol. 88, No. 11 (7 pages).

Jarde, A., et al., "Effectiveness of progesterone, cerclage and pessary for preventing preterm birth in singleton pregnancies: a systematic review and network meta-analysis," BJOG: An International Journal of Obstetrics and Gynaecology, 2017 (14 pages).

Jin, X., et al., "Cervical Pessary for Prevention of Preterm Birth: a Meta-Analysis," www.nature.com/scientificreports.com, 2017 (6 pages).

Kalinka, J., et al., "Rupture of the cervix during pregnancy after cervical pessary insertion for preventing preterm birth," The Journal of Obstetrics and Gynaecology Research, vol. 42, No. 12, 2016 (4 pages).

(56) References Cited

OTHER PUBLICATIONS

Karisallen, L., et al., "Retrospective Cohort Study of Cervical Pessary Use in Women with Short Cervix at Risk of Preterm Delivery," J. Obstet. Gynaecol Can., 2017 (6 pages).
Khalifeh, A., et al., "Not transabdominal!", American Journal of Obstetrics & Gynecology, Dec. 2016 (7 pages).
Klein, K., et al., "Vaginal micronized progesterone and risk of preterm delivery in high-risk twin pregnancies: secondary analysis of a placebo-controlled randomized trial and meta-analysis," Ultrasound Obstet. Gynecol, 2011 (7 pages).
Koullali, B., et al., "A multi-centre, non-inferiority, randomised controlled trial to compare a cervical pessary with a cervical cerclage in the prevention of preterm delivery in women with short cervical length and a history of preterm birth—PC Study," BMC Pregnancy and Childbirth, 2017 (9 pages).
Liem, S., et al., "Cervical pessaries to prevent preterm birth in women with a multiple pregnancy: a per-protocol analysis of a randomized clinical trial," AOGS, 2016 (8 pages).
Makrydimas, G., "Vaginal progesterone, cerclage or cervical pessary for preventing preterm birth in asymptomatic singleton pregnant women with history of preterm birth and a sonographic short cervix," Ultrasound Obstet. Gynecol, 2013 (1 page).
Marasinghe, J., "Cervical Pessary and Vaginal Progesterone in Twin Pregnancies with a Short Cervix:", Obstet. Gynecol, Aug. 2016 (1 page).
Melendez, J., et al., "Cervical pessary in pregnant women with a short cervix," Lancet. Sep. 2012 (2 pages).
Mendoza, M., et al., "Modification of cervical length after cervical pessary insertion: correlation weeks of gestation," The Journal of Maternal-Fetal & Neonatal Medicine, Aug. 28, 2016 (7 pages).
Merced, C., et al., "Cervical pessary for preventing preterm birth in twin pregnancies with maternal short cervix after an episode of threatened preterm labor: randomised controlled trial," Am. J. Obstet. Gynecol., Feb. 28, 2019 (14 pages).
Nicolaides, K., et al., "A Randomized Trial of a Cervical Pessary to Prevent Preterm Singleton Birth," The New England Journal of Medicine, Mar. 17, 2016 (9 pages).
Nicolaides, K., et al., "Cervical pessary placement for prevention of preterm birth in unselected twin pregnancies: a randomized controlled trial," Am. J. Obstet. Gynecol., Jan. 2016, (9 pages).
Pratcorona, L., et al., "Cervical pessary to reduce preterm birth less than 34 weeks of gestation after an episode of preterm labor and a short cervix: a randomized controlled trial," Amer. J. Obstet. Gynecol., Jul. 2018 (16 pages).
Saccone, G., et al., "Cervical Pessary for Preventing Preterm Birth in Singleton Pregnancies with Short Cervical Length," J. Ultrasound Med. Aug. 2017, (9 pages).
Saccone, G., et al., "Cervical Pessary for Preventing Preterm Birth in Twin Pregnancies with Short Cervical Length: a systematic review and meta-analysis" J. Matern. Fetal Neonatal Med. Dec. 2017 (9 pages).
Saccone, G., et al., "Effect of Cervical Pessary on Spontaneous Preterm Birth in Women with Singleton Pregnancies and Short Cervical Length—A Randomized Clinical Trial," JAMA, Dec. 2017 (8 pages).
Saccone, G., et al., Effects of Exercise During Pregnancy in Women with Short Cervix: Secondary analysis from the Italian Pessary Trial in Singletons, Eur. J. Obstet. Gynecol. Reprod. Biol. Oct. 2018, (6 pages).
Sharp, A., et al., "Provision and practice of specialist preterm labour clinics: a UK survey of practice," BJOG.org, Mar. 2014 (5 pages).
Stricker, N., et al., "Vaginal progesterone combined with cervical pessary: A chance for pregnancies at risk for preterm birth?", Am. J. Obstet. Gynecol. Jun. 2016 (11 pages).
Tajik, P., et al., A multivariable model to guide the decision for pessary placement to prevent preterm birth in women with a multiple pregnancy: a secondary analysis of the ProTWIN trial, Ultrasound Obstet. Gynecol, Jul. 2016 (8 pages).
Thangatorai, R., et al., "Cervical pessary in the prevention of preterm births in multiple pregnancies with a short cervix: PRISMA compliant systematic review and meta-analysis," J. Matern. Fetal Neonatal Med. Jun. 2018 (14 pages).
Van 'T Hooft, J., et al., "Pessary for prevention of preterm birth in twin pregnancy with short cervix: 3-year follow-up study," Ultrasound Obstet. Gynecol. May 2018 (8 pages).
Van Zijl, M. et al., "Pessary or Progesterone to Prevent Preterm delivery in women with short cervical length: the Quadruple P randomized controlled trial," BMC Pregnancy Childbirth Sep. 2017 (8 pages).
Van Zijl, M. et al., "Prevention of preterm delivery: current challenges and future prospects," Int. J. Womens Health, Oct. 2016, (13 pages).
Vintzileos, A.M., et al., "Interventions for women with mid-trimester short cervix: which ones work?", BJOG, Jul. 2017 (6 pages).
Cross, R., "Treatment of habitual abortion due to cervical incompetence", Lancet 1959:2:127.
Kindinger, L., et al., "The interaction between vaginal microbiota, cervical length, and vaginal progesterone treatment for preterm birth risk," Microbiome (2017) (14 pages).
Iams, J.D., et al., "The length of the cervix and the risk of spontaneous premature delivery", N. Engl. J. Med. 1996:334:567-572.
Berghella, V., "Universal Cervical Length Screening for Prediction and Prevention of Preterm Birth," Obstetrical and Gynecological Survey, vol. 67, No. 10 (2012).
Liem, S.M.S, et al., "Cervical Pessaries for the Prevention of Preterm Birth: A Systematic Review". Obstetrics and Gynecology International 2013: 1-10.
McDonald, I.A., "Suture of the cervix for inevitable miscarriage", J. Obstet. Gynaecol. Br. Emp 1957:64:712-714.
Boiko, V., et al., "The problem of miscarriage in multiple pregnancy," 2018, Sumy State University, Sumy, Ukraine, 13 pages.
Oster, S., et al., "Treatment of the incompetent cervix with the Hodge pessary", Obstet. Gynecol. 1966:28:206-208.
Shirodkar, V.N., "A new method of operative treatment for habitual abortion in the second trimester of pregnancy", Antiseptic 1955:52:299.
Vitsky, M., "Simple treatment of the incompetent cervical os", Am.J.Obst. & Gynec. Jun. 1961, vol. 81, No. 6, 1194-1197 (4 pages).
Daskalakis, G., et al., "Safety and efficacy of the cervical pessary combined with vaginal progesterone for the prevention of spontaneous preterm birth," Journal of Perinatal Medicine, Jul. 26, 2018 (8 pages).
Louras, G.M., et al., "Successful pregnancy with the use of vaginal pessary in a patient with a very short cervix," Societa Editrice Universo, Clin. Ter. (2014) 299-301 (5 pages).
Willan, A. R., et al., "Accounting for treatment by center interaction in sample size determinations and the use of surrogate outcomes in the pessary for the prevention of preterm birth trial: a simulation study," Trials, Jul. 2016 (8 pages).
Yuce, T., et al., "Pessary use in pregnant women with short cervix", J. Turk. Ger. Gynecol Assoc. Jan. 2016 (3 pages).
Martinelli, P. et al., "Cervical Pessary and Spontaneous Preterm Birth," Journal of American Medical Association, May 1, 2008 (2 pages).
Bayer, V.H., "Various New Aspects for Prevention and Therapy of Impending Premature Birth," Zentralblatt fur Gynakologie, vol. 99, Issue 9, pp. 547-551 [no English translation].
Prevention of Preterm birth in Twins with Short Mid-Trimester Cervical Length Less than 25MM-combined Treatment with Arabin's Cerclage Pessary and Intravaginal Micronized Progesterone Compared with Conservative Treatment, 2018 (5 pages) [no English translation].
Javert, O.S., et al., "Treatment of the incompetent cervix with the Hodge Pessary," Obstet. Gynecol. Aug. 28, 1966(4 pages).
Gyselaers, W., et al., "Gestational hypertensive disorders show unique patterns of circulatory deterioration with ongoing pregnancy," www.physiology.org/journal/ajpregu At Washington University on Feb. 13, 2019 (51 pages).
Malinova, M., "Clinical treatment in Shorten Cervix" 2013 (10 pages) [no English translation].

(56) References Cited

OTHER PUBLICATIONS

"First year experience using arabin cervical pessary with intravaginal micronized progesterone for the prevention of preterm birth in patients with mid-trimester short cervix," (2014) [no English translation].

Arabin, B., et al., "Is treatment with vaginal pessaries an option in patients with a sonographically detected short cervix?", J. Perinat. M.Ed. 31 (2003) pp. 122-133 912 pages).

Brun, S., "Cervical pessary and spontaneous preterm birth," Elsevier (2016) 45, 1324-1336 (13 pages) [no English translation].

Monfrance, M., et al., "Pessary placement in the prevention of preterm birth in multiple pregnancies: a propensity score analysis," Elsevier, vol. 197 (2016) 76-77 (6 pages).

Dunn, L.J, et al., "Maternal death following suture of an incompetent cervix during pregnancy", Am J Obstetric Gynecol 1962:84:114.

Leduc, L., et al., "Successful treatment with the Smith-Hodge pessary of cervical incompetence due to defective connective tissue in Ehlers-Danlos syndrome", Am J Perinatol 1992:9:25-27.

Newcomer, J., "Pessaries for the treatment of incompetent cervix and premature delivery", Obstet Gynecol Survey 2000:55:443-448.

PCT Search Report and Written Opinion of corresponding PCT appl. No. PCT/US/2020/015789 dated May 26, 2020.

Ge, Weirong, et al. "Sensor Technology to Track Forces, Placement and Positioning of Arabin Pessary," 2017 Eleventh International Conference on Sensing Technology, IEEE, Dec. 4, 2017, 4 pages.

Patent Cooperation Treaty, International Search Report and Written Opinion issued for PCT Application No. PCT/US2021/071684, dated Jan. 7, 2022, 16 pages.

\* cited by examiner

WIRELESS POWER FOR PESSARY DEVICE

CROSS-REFERENCE TO RELATED PATENT APPLICATIONS

The present application is a continuation-in-part (CIP) of U.S. patent application Ser. No. 16/444,279 to Gei et al. filed on Jun. 18, 2019 and entitled "Pessary Device and Methods for Preventing Premature Births," the disclosure of which is incorporated by reference herein in its entirety.

FIELD OF THE INVENTION

The present disclosure relates generally to a pessary device and methods for preventing premature births. More particularly, the present disclosure related to a pessary device for retaining the cervix during pregnancy to prevent premature births and associated methods.

BACKGROUND

Preterm birth (PTB) is the leading cause of perinatal morbidity and mortality in the United States. Despite efforts to decrease the incidence of this problem over the last few decades, the rate of preterm delivery remains high.

The PTB rate rose in 2017, and about 1 in 10 babies (10%) was born too early in the United States. Because of this high incidence, the prevention of preterm delivery is a major area of concern in contemporary obstetrics, as well as a societal necessity. According to the Centers of Disease Control (CDC) reducing PTB is a national public health priority.

Cervical Shortening and PTB

In 1996, it was demonstrated that the risk of preterm delivery is inversely proportional to the length of the cervix on transvaginal sonography between 24 and 28 weeks of gestation within an unselected United States population. (Jams J D, Goldenberg R L, Meis P J, et al: *The Length of the Cervix and the Risk of Spontaneous Premature Delivery*, N Engl J Med 1996:334:567-572)

Cervical insufficiency (formerly called "incompetence") as used herein means the inability of the uterine cervix to retain an intrauterine pregnancy until viability of the fetus. It is usually characterized as an acute, painless second trimester dilatation of the cervix resulting in premature delivery. A short cervix as used herein means a shortened anatomical length of the cervix as measured along the longitudinal axis of the cervix. It is usually found in the mid-trimester of the pregnancy and detected either by ultrasound or digital examination. A short cervix can be a hallmark finding used as a surrogate marker for diagnosis of cervical insufficiency. This is particularly relevant in those women with a previous history of pregnancy loss or preterm delivery. It has been appealing to clinicians to consider a mechanical method by which to strengthen the cervix, keep it closed, and increase its length in the hope of preventing preterm delivery.

Since the introduction of cerclage, or a cervical stitch, by Shirodkar (Shirodkar V N: *A New Method of Operative Treatment for Habitual Abortion in the Second Trimester of Pregnancy, Antiseptic* 1955:52:299) and McDonald (McDonald I A: *Suture of the Cervix for Inevitable Miscarriage, J Obstet Gynaecol Br Emp* 1957:64:712-714) in the 1950's, this treatment modality has been submitted to multiple study trials with mixed results. Furthermore, recently the use of progesterone for the treatment of a short cervix is also under intense research evaluation.

Cervical insufficiency and cervical shortening leading to preterm delivery are overlapping conditions in the spectrum of cervical shortening at various gestational ages. The distinction is sometimes difficult to make and is subjective.

Cervical Physiology

During the pregnancy the cervical canal normally stays tightly closed with a cervical mucus plug (CMP) filling its lumen. It is hypothesized that impairment of the CMP, for example, by cervical shortening, can lead to an ascending infection and preterm delivery.

Pessaries

As used herein, a pessary is a removable device placed into the vagina for therapeutic purposes. Pessaries currently come in a wide range of shapes and sizes and are typically used for pelvic organ prolapse. Typically, they are of a ring-like shape which circumscribes the cervix and performs similar to a cerclage. (See, McDonald)

The thought behind the mechanism of action of the pessary was proposed by Vitsky in 1961. He described the pregnancy as causing a steady and mounting pressure on the internal orifice of the cervix ("internal OS") and noted that it is irrelevant whether this is due to cervical trauma or congenital causes. (Vitsky M: *Simple Treatment of the Incompetent Cervical Os, Am J Obstet Gynecol* 1961:81: 1194-1197). The pattern is the same, and eventually the membranes weaken by sacculation and rupture, and, in due time, labor with expulsion of the uterine contents. The cervix with its axis directly and centrally aligned into the non-resistant vagina, lends itself to its own dissolution. Vitsky suggested that a device that can alter this collineation so that the force is directed inward would be helpful. He suggested that a pessary might have merit in this situation, as it can change the inclination of the cervical canal and can also compress the cervical canal in the earlier part of pregnancy.

Pessaries for the Prevention of PTB

Early reports on the use of pessaries for the prevention of spontaneous PTB (sPTB) used models originally designed to treat genital prolapse.

In 1959, Cross described his experience using a ring pessary in 13 patients with either a history of cervical lacerations, cervical incompetence or uterus didelphus. (Cross R. G: *Treatment of Habitual Abortion due to Cervical Incompetence, Lancet* 1959:2:127) Vitsky described the use of a Hodge pessary in seven patients and in a further 14 of his colleagues' patients, postulating that the reduction of pressure on the internal os prevented the protrusion of membranes. (*Vitsky M Simple treatment of the incompetent cervical os. Am J Obstet Gynecol* 1961; 81:1194). He also suggested that a pessary might change the inclination of the cervical canal and compress the cervix, but this was never tested. Considering the large openings of the Hodge and ring pessaries, this hypothesis does not seem likely. Oster and Javert also used a Hodge pessary in 29 patients with 'cervical incompetence' defined by different criteria, arguing that treatment with a pessary would be superior to surgical cerclage due to the reduced risk of bleeding or maternal sepsis. (Oster S, Javert C. T. *Treatment of the Incompetent Cervix with the Hodge Pessary, Obstet Gynecol* 1966:28: 206-208). The Hodge pessary encompasses the cervix and compresses the cervical canal, and as such may prevent the loss of the CMP. The pessary also alternates the inclination of the cervical canal and corrects the incompetent cervix pointing forward in the axis of the vagina. It relieves direct pressure on the internal OS by distributing the weight of the pregnant uterus onto the vaginal floor, the retro-symphyseal osteomuscular structures, and the Douglas cavity and, as such, may prevent premature dilatation of the cervix and premature rupture of the membranes. Furthermore, it blocks the fetal head from descending and pressing on the internal ostium (a/k/a internal orifice or internal os).

The cervical pessary is relatively noninvasive and is not an operator-dependent intervention. It can be easily placed or removed in an outpatient clinic and does not require anesthesia. With speculum examination, the cervix is identified to determine an appropriate pessary size. The silicon Arabin pessary, available for example from Dr. Arabin GmbH & Co. KG of Witten Germany as the Cerclage and Cerclage Perforated Pessary models, are popular and come in different sizes of diameter and height. They are non-collapsible with limited bending and fit high around the cervix so that smaller inner diameter of the prior art ring structure encompasses or circumscribes the cervix. After placement the patient is briefly observed to ensure there is no discomfort, vaginal bleeding, or uterine activity.

Recent meta-analysis of the randomized trials identified six trials evaluating the use of pessary with cervical length (CL)<25 mm (1,992 using pessary devices vs 999 controls). Four trials administrated vaginal progesterone to the pessary and the control group. There were no significant differences seen in the rates of spontaneous PTB (sPTB) or any PTB prior to 28, 34, or 37 weeks. There was high heterogeneity noted for sPTB <34 weeks. Three trials found no significant reduction in sPTB rate <34 weeks, while two trials demonstrated a significant reduction (6.3% vs 26.8%; 7.3% vs 15.3%, respectively). (Liem S M et al. *Cervical pessaries for the prevention of preterm birth. A systematic review.* Obstetrics and Gynecology International 2013; 2013 Article 576723). Women with pessaries were more likely to report increased vaginal discharge at follow up visits. Only 5.4% requested removal of the pessary. There were no significant differences in delivery or neonatal outcomes. Based on single gestations with short cervical length randomized to cervical pessary, the investigators concluded that there was not a significant difference in rates of PTB between the pessary group and the control group. However, these results demonstrate the large heterogeneity in both the statistical analysis as well as in the results of individual trials.

Thus, there are certain shortcomings of the prior art pessary devices. First, the need exists for an improved pessary that serves to extend the length of the cervix in women at risk of preterm pregnancies. There is also a need to configure the pessary so that degradation of vaginal flora is minimized thereby decreasing the chances of infection within the birth canal during gestation and at birth. Further, an improved pessary is needed to retain, and preferably enhance, the radial forces on the circumscribed cervix when the patient is standing. Moreover, the pessary should be made of a biologically compatible, pliable, collapsible and consistent material which maximizes the ease of installation, retention and removal. All this should be done while continuing to maximize patient comfort.

It should be understood that the above-described features, capabilities and disadvantages are provided for illustrative purposes only and are not intended to limit the scope or subject matter of the appended claims or those of any related patent application or patent. Thus, none of the appended claims or claims of any related application or patent should be limited by the above discussion or construed to address, include or exclude each or any of the above-cited features, capabilities or disadvantages merely because of the mention thereof herein.

BRIEF SUMMARY OF THE DISCLOSURE

The present disclosure is a pessary used to prevent premature birth of a fetus and, in particular, two pathological conditions of pregnancy known as isthmico-cervical insufficiency and cervical shortening, both of which are associated with increased risks for pregnancy loss and/or premature deliveries of babies.

The pessary of the present disclosure comprises a sleeve configured to circumscribe the cervix. At the top or superior end of the sleeve the pessary includes an annular member having a superior surface and an inferior surface. The superior surface of the annular member engages the vagina proximate the cervix. The pessary further includes a ring attached at the outer edge of the annular member which also engages the vagina. In this manner, upon final placement of the pessary within the vagina at least a portion of the interior surface of the sleeve contacts a portion of the cervix and at least a portion of the superior surface of the annular member and at least a portion of the outer surface of the ring contact a portion of the vagina. This configuration serves to lengthen the cervix.

In another embodiment of the present disclosure the sleeve, annular member, and ring include a plurality of apertures which provide fluid communication throughout the pessary in order to permit hydration of the cervix and vagina and drainage of vaginal discharge resulting from epithelial tunrover.

In yet another embodiment of the present disclosure, the longitudinal length of the sleeve is greater than the longitudinal length of the ring. Preferably, the longitudinal length of the sleeve is at least 50% greater than the longitudinal length of the ring, and more preferably, the longitudinal length of the sleeve is at least twice the longitudinal length of the ring.

In a further yet embodiment of the present disclosure, the pessary includes at least one sensor preferably mounted proximate the sleeve and in contact with the cervix. In this manner, the sensor may receive a signal indicative of a physiological condition such as premature contraction. It may also be configured to generate a signal, for example, such as an electrical current to inhibit the premature contractions of the uterus.

In yet a further embodiment of the present invention, portions of the pessary such as the sleeve, annular member, and/or the ring may include a coating of a biologically beneficial medication, such as progesterone, prostaglandin inhibitors and other beneficial drugs. Alternatively, the pessary may be manufactured of the material comprising the medical-grade (e.g., biocompatible) polymeric material such as silicone and/or polyurethane impregnated with biologically beneficial medication which is intended for slow release onto the cervix or within the vagina and/or uterus.

In another embodiment of the present disclosure, the pessary may be wirelessly powered, wirelessly charged, and/or wirelessly communicated with by receiving electromagnetic waves from a master device by coupling a receiving structure of the pessary to a transmitting structure of the master device. The master device may charge a battery, capacitor, or other energy storage device in the pessary device and/or may be used to directly power electrical circuitry in the pessary device. A pessary of any of the embodiments disclosed herein may include a power transceiving structure affixed to or embedded within the pessary and configured to receive wireless power transmissions by coupling the power transceiving structure with electrical circuitry of the pessary. The electrical circuitry may be configured to monitor conditions in a vicinity of the pessary indicative of a preterm birth of a fetus using power received from the power transceiving structure. Various structures for a power transceiving structure are described herein, and the pessary device may include structures for near-field (non-radiative) or far-field (radiative) power transfer techniques including inductive coupling with a master device, capacitive coupling with a master device, magnetodynamic coupling with a master device, radio frequency (RF) signal transfer with a master device, and/or light (e.g., laser) signal transfer with a master device. Near-field coupling may enable wireless transfer over short to medium distances, such as from nearly contacting to several feet, which may be useful with master devices such as a pillow, pelvic belt, or table-top device or appliance as described in embodiments herein. Far-field coupling may enable wireless transfer over medium to long distances, such as from one foot to tens of feet, which may be useful with master devices such as a table-top device or appliance. In some embodiments, the electromagnetic fields transferred between the pessary device and a master device may have a circular polarization to improve efficiency of the transfer. In some embodiments, the pessary device may also transmit power to receiver devices through the wireless power transceiver structure.

Accordingly, the present disclosure includes features and advantages which are believed to enable it to advance medical technology. Characteristics and advantages of the present disclosure described above, and additional features and benefits will be readily apparent to those skilled in the art upon consideration of the following detailed description of various embodiments and referring to the accompanying drawings.

BRIEF DESCRIPTION OF THE DRAWINGS

The following figures are part of the present specification, included to demonstrate certain aspects of various embodiments of this disclosure and referenced in the detailed description herein.

DETAILED DESCRIPTION OF PREFERRED EMBODIMENTS

Figure 1:
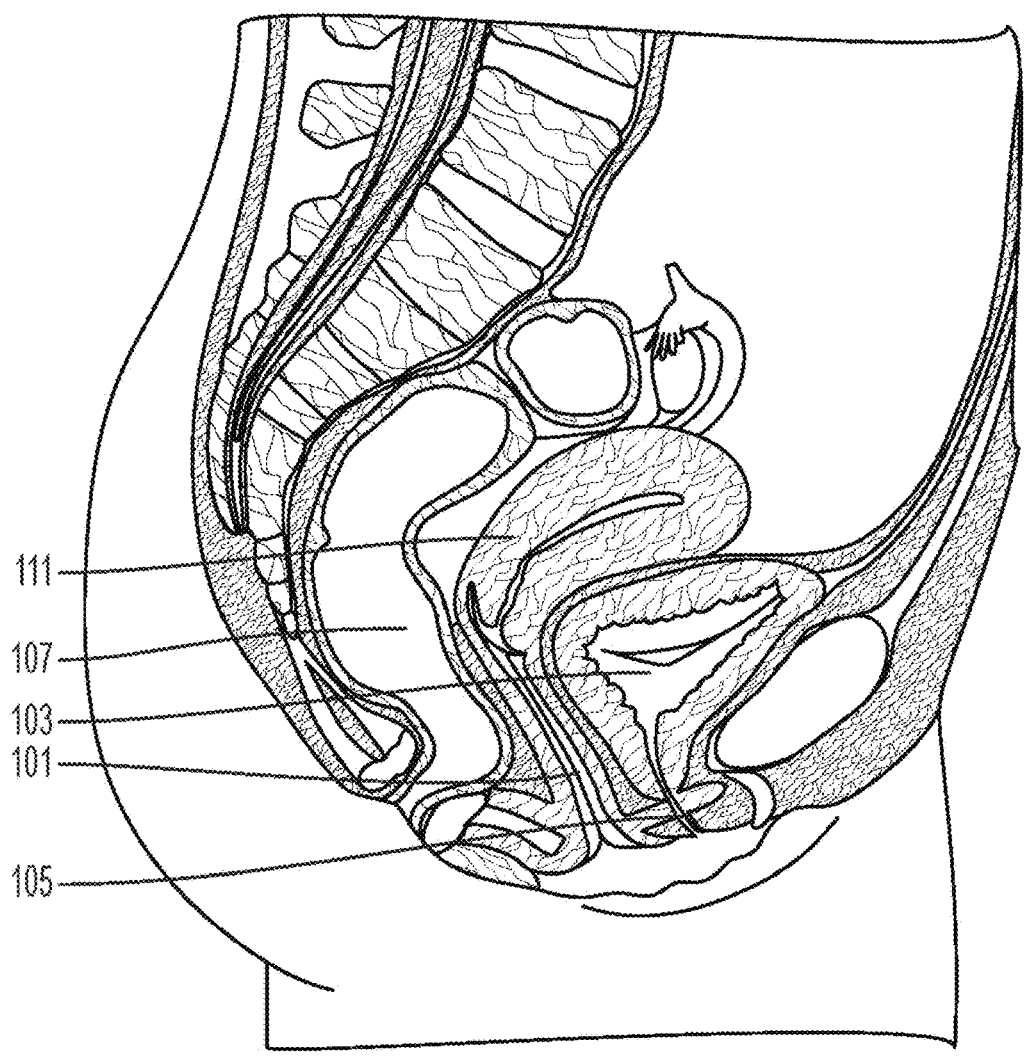
FIG. 1 is an anatomical view of the abdominal portion of a normal female.

The present invention now will be described more fully hereinafter with reference to the accompanying drawings, in which at least some preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Characteristics and advantages of the present disclosure and additional features and benefits will be readily apparent to those skilled in the art upon consideration of the following detailed description of exemplary embodiments of the present disclosure and referring to the accompanying figures. It should be understood that the description herein and appended drawings, being of example embodiments, are not intended to limit the claims of this patent application or any patent or patent application claiming priority hereto. On the contrary, the intention is to cover all modifications, equivalents and alternatives falling within the spirit and scope of this disclosure or any appended claims. Many changes may be made to the particular embodiments and details disclosed herein without departing from such spirit and scope.

In showing and describing preferred embodiments in the appended figures, common or similar elements are referenced with like or identical reference numerals or are apparent from the figures and/or the description herein. The figures are not necessarily to scale and certain features and certain views of the figures may be shown exaggerated in scale or in schematic in the interest of clarity and conciseness.

As used herein and throughout various portions (and headings) of this patent application, the terms "invention", "present invention" and variations thereof are not intended to mean every possible embodiment encompassed by this disclosure or any particular claim(s). Thus, the subject matter of each such reference should not be considered as necessary for, or part of, every embodiment hereof or of any particular claim(s) merely because of such reference. The terms "coupled", "connected", "engaged", "attached", and the like, and variations thereof, as used herein and in the appended claims are intended to mean either an indirect or direct connection or engagement. Thus, if a first device couples to a second device, that connection may be through a direct connection, or through an indirect connection via other devices and connections.

Certain terms are used herein and in the appended claims to refer to particular components. As one skilled in the art will appreciate, different persons may refer to a component by different names. The use of a particular or known term of art as the name of a component herein is not intended to limit that component to only the known or defined meaning of such term (e.g. bar, member, connector, rod, cover, panel, bolt, screw, and pin). Further, this document does not intend to distinguish between components that differ in name but not function. Also, the terms "including", "comprising", and "having" are used herein and in the appended claims in an open-ended fashion, and thus should be interpreted to mean "including, but not limited to . . . ." Further, reference herein and in the appended claims to components and aspects in a singular tense does not necessarily limit the present disclosure or appended claims to only one such component or aspect, but should be interpreted generally to mean one or more, as may be suitable and desirable in each particular instance.

As used herein, the terms "elongated" and variations thereof mean having an average length that is greater than its average width. As used herein, the terms "substantially", "generally" and variations thereof means and includes (i) completely, or 100%, of the referenced parameter, variable or value, and (ii) a range of values less than 100% based upon the typical, normal or expected degree of variation or error for the referenced parameter, variable or value in the context of the particular embodiment or use thereof, such as, for example, 90-100%, 95-100% or 98-100%.

Figure 2:
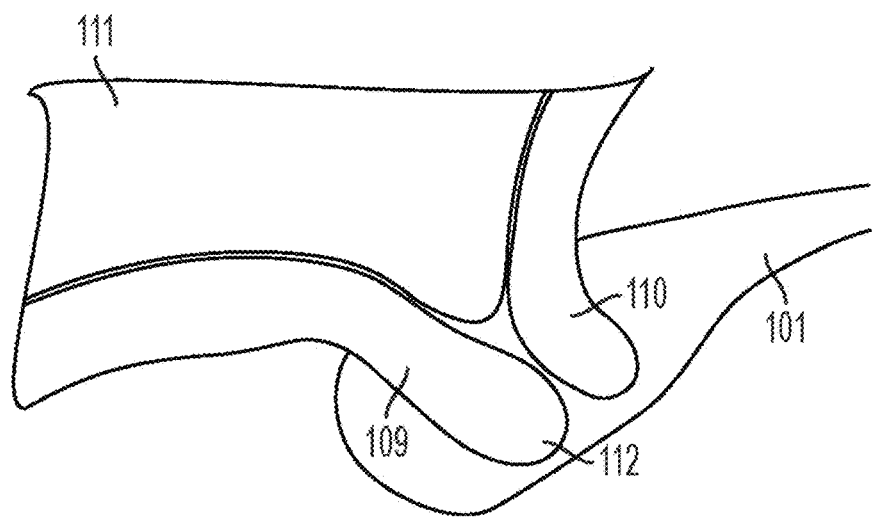
FIG. 2 is a simplified anatomical schematic of a cervix extending from a uterus into a vagina.

Referring to FIG. 1, a cross-sectional female abdominal sketch is shown. Vagina 101 is shown relative to bladder 103, urethra 105, and rectum 107. Referring now also to FIG. 2, cervix 109 is positioned descended from uterus 111. As noted above, while a cervical pessary is a relatively noninvasive, the present invention is pliable, collapsible, elastic, and self-expandable conserving its original shape. In addition, the present invention conforms to the anatomy of the cervix 109 proximate to bladder 103, urethra 105 and rectum 107. These properties facilitate placement and ensure patient comfort during retention around the cervix.

Figure 3:
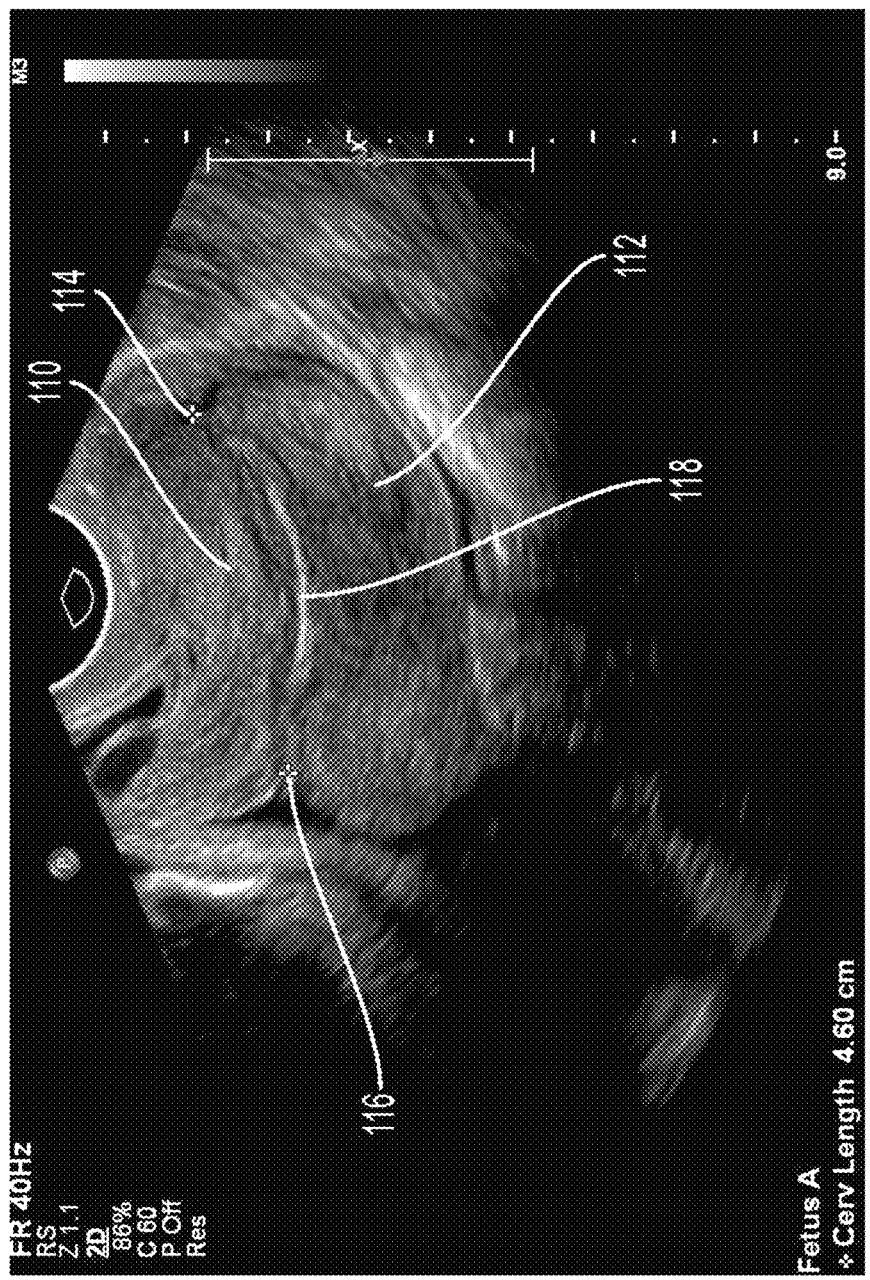
FIG. 3 is an ultrasound of a normal cervical anatomy.

Referring to FIG. 3, an ultrasound of a normal cervical anatomy is shown. Cervix 109 comprises an anterior lip 110 and a posterior lip 112. The external orifice (EOS) 114 and internal orifice (IOS) 116 of the of the uterus wall are also identified. Endocervical canal 118 is shown between anterior lip 110 and posterior lip 112.

Figure 4:
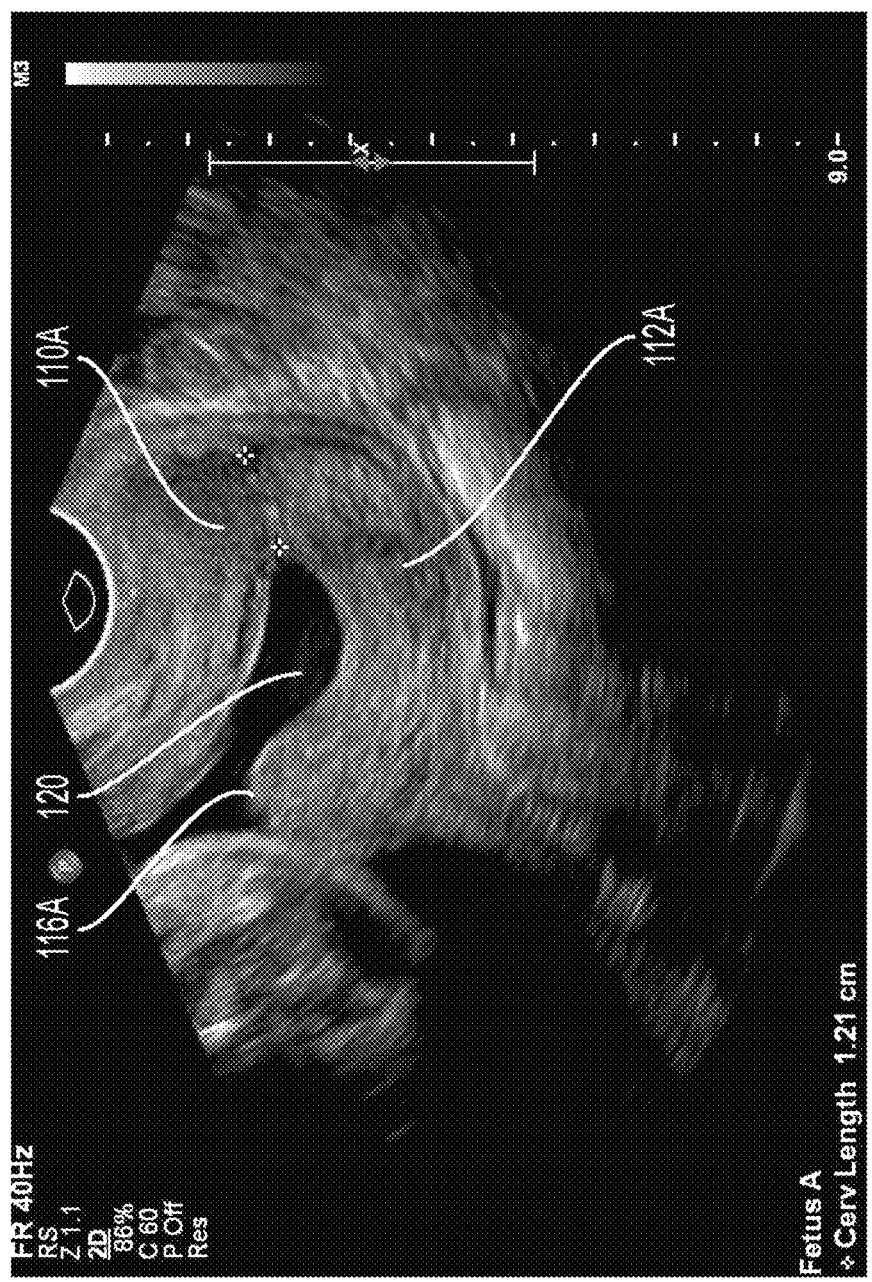
FIG. 4 is an ultrasound of a shortened anatomical cervix.

Referring now to FIG. 4, an ultrasound of an abnormally short cervix is shown having an anterior lip 110A displaced from posterior lip 112A resulting in an internal funnel 120 of the proximate the internal OS 116A. Such a funnel 120 results in a shortening of the cervix which is inversely proportional to the length of funnel 120. That is, the longer the length of funnel 120, the shorter the length of the cervix.

Figure 5:
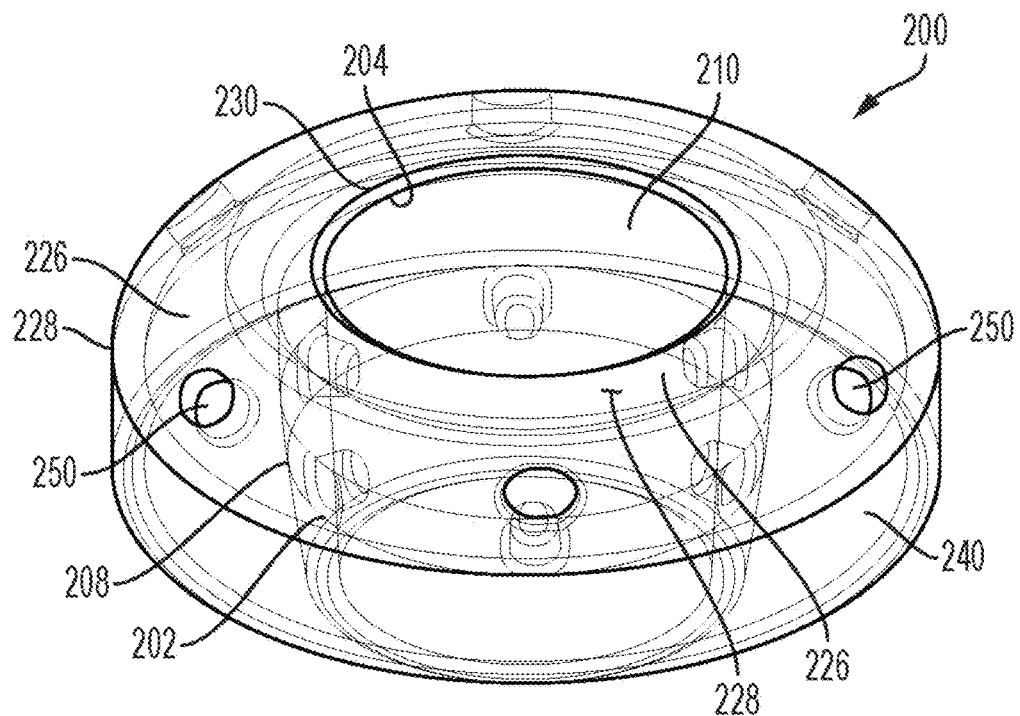
FIG. 5 is an isometric view of the superior side of the present invention.
Figure 6:
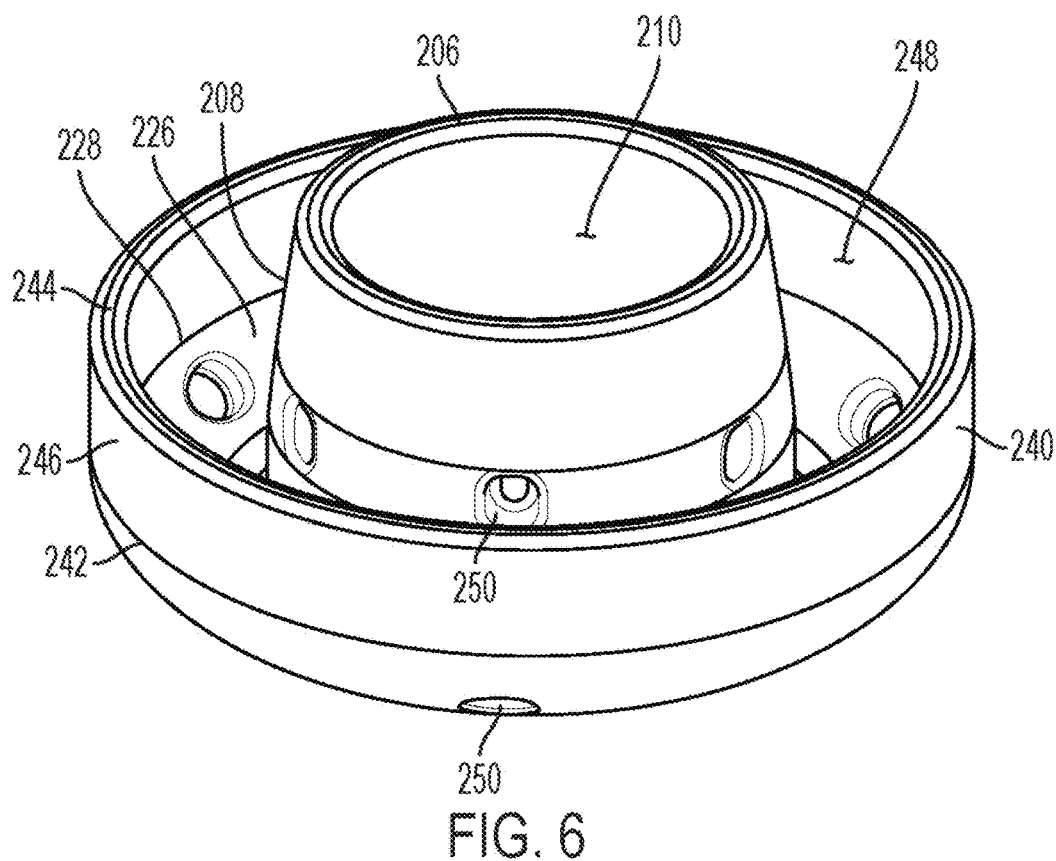
FIG. 6 is an isometric view of the inferior side of the present invention.
Figure 7:
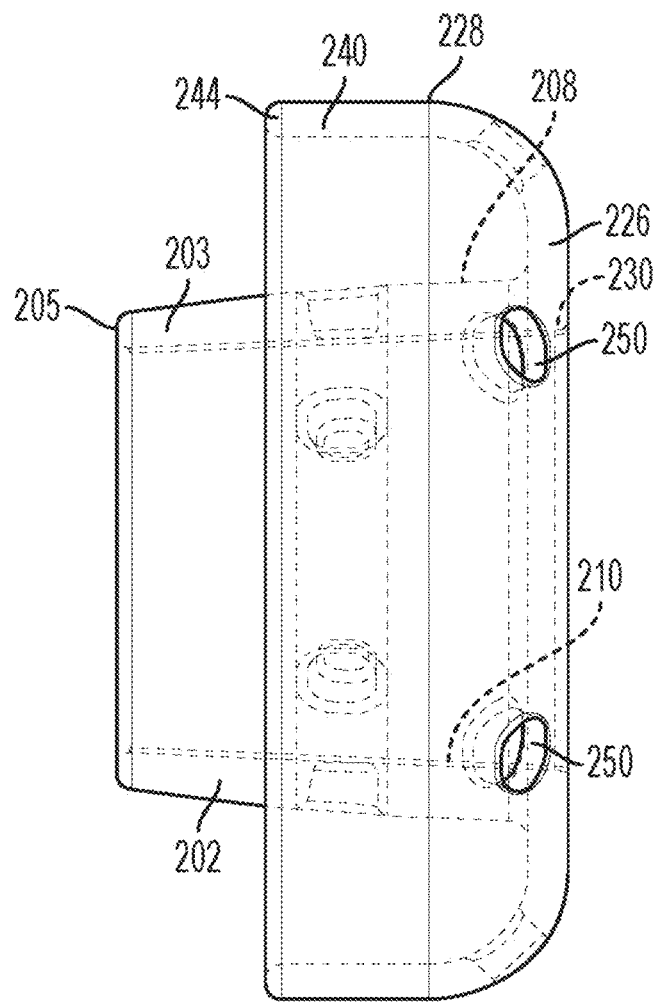
FIG. 7 is a side view of the present invention.

Referring to FIGS. 5-7, the present invention comprises a pessary device 200 having an internal sleeve 202 having a first edge 204, a second edge 206, an outer surface 208 and an interior surface 210. The present invention also includes an annular member or portion 226 having an outer edge 228 and an inner edge 230. Sleeve 202 is supported by annular member 226 at first edge 204 by inner edge 230 of annular member 226. The present invention also includes a ring 240 having first edge 242, a second edge 244, an outer surface 246 between the first and second edges 242/244, and an interior surface 248 between edges first and second edges 242/244. First edge 242 of ring 240 is attached to outer edge 228 of annular member 226.

The length of sleeve 202 between first edge 204 and second edge 206 is preferably greater than the distance between first and second edges 242/244 of ring 242. More preferably, the length of sleeve 202 between first edge 204 and second edge 206 is at least 50% greater than the distance between first and second edges 242/244 of ring 242. Even more preferably, the length of sleeve 202 between first edge 204 and second edge 206 is at least 75% greater than the distance between first and second edges 242/244 of ring 242. Most preferably, the length of sleeve 202 between first edge 204 and second edge 206 is at least twice the distance between first and second edges 242/244 of ring 242.

Referring in particular to FIG. 7, wall 203 of sleeve 202 may be tapered slightly as shown, so that at least inner surface 210 tapers slightly inwardly toward the cervix once placed within a patient. The outer surface 208 may be tapered slightly inwardly as shown, particularly proximate edge 205. In this manner, the lower or inferior portion of wall 203 is slightly more pliable and may more easily grasp the posterior and anterior lips 110/112 of cervix 109 and retains same in place due the anatomy of the patient's cervix and the transmission of radial forces from the vaginal muscle as discussed below.

The present invention may include one or more apertures 250 which serve to prevent the accumulation of fluid and to allow for lubrication and hydration of the roof of the vaginal walls. Interior surface 210 of sleeve 202 contacts and circumscribes cervix 109 once installed in the patient. Apertures 250 passing through sleeve 202 serve to allow for lubrication and hydration of the cervix, and drainage of cellular debris. As interior surface 210 is intended to contact the outer portion of cervix 109, it transmits an elastic load to stabilize and occlude cervical canal 118. Interior surface 210 of sleeve 202 has more surface area than a simple ring-shaped prior art pessary device which thereby makes the present invention more effective in transmitting an elastic force to the cervix, and in supporting the cervix.

FIG. 5 shows the superior view of device 200 with dashed lines reflecting internal geometry. FIG. 6 is an inferior view of device 200, and FIG. 7 is a side view of device 200. Elements of the present invention are shown with similar numerals to reflect the same elements as discussed above.

Figure 8:
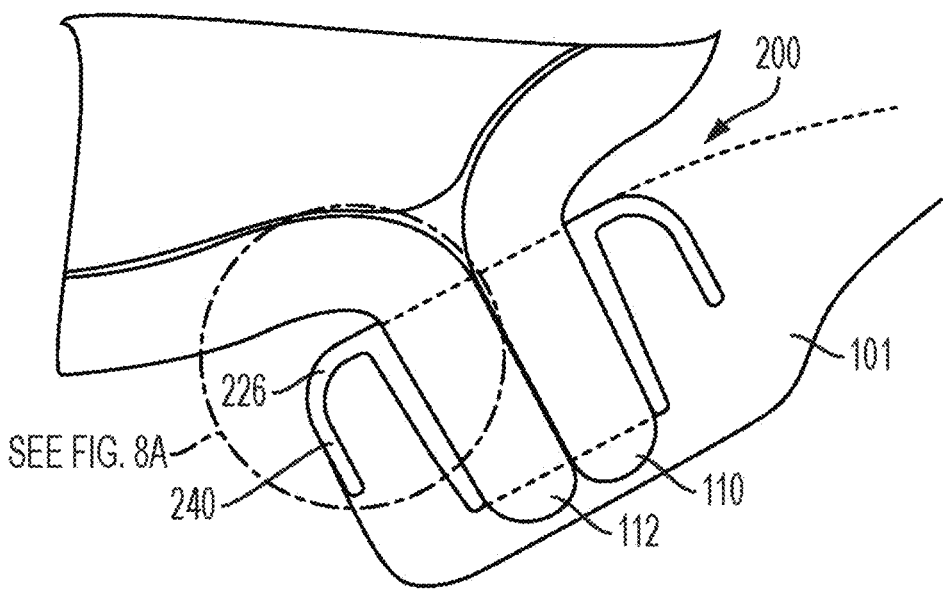
FIG. 8 is a sketch of the present invention in final position at a cervix within a vagina.
Figure 8A:
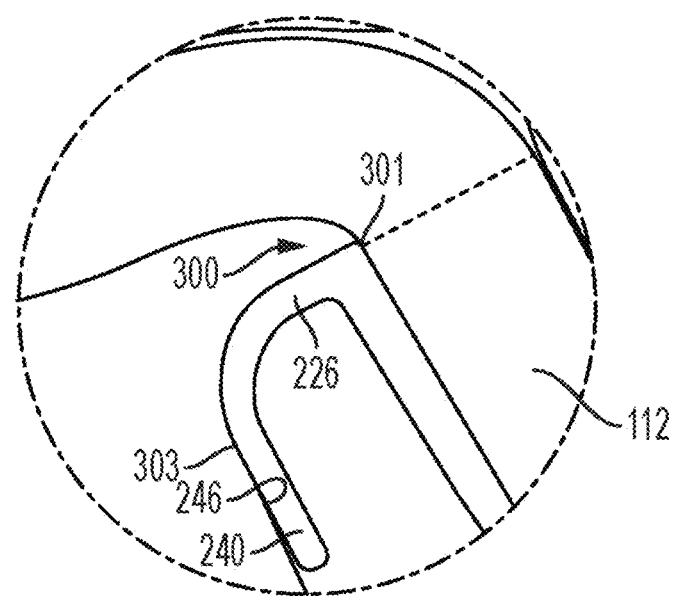
FIG. 8A is a detailed view of a portion of FIG. 8.

Referring now to FIGS. 8 and 8A, the shape of device 200 is selected so that annular member 226 contacts cervical vaginal interface 300 with upper convexity 301 of the shoulder of annular member 226. Thus, outer surface 246 of ring 240 fit snugly against the vaginal ceiling 303. This serves to provide additional support for device 200 and enhance patient comfort.

Figure 9:
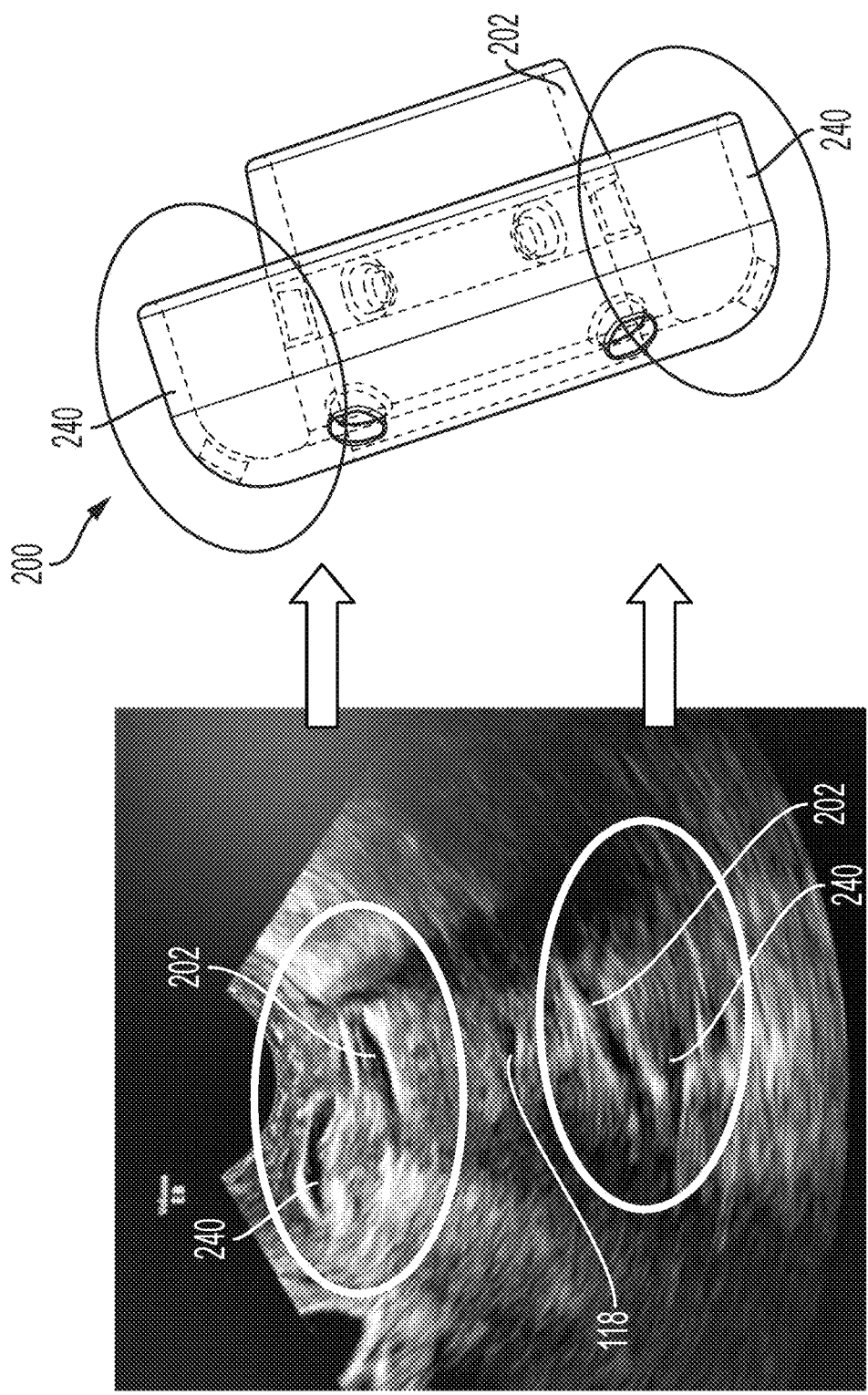
FIG. 9 is an ultrasound of the present invention in place circumscribing the cervix within the vagina.

Referring now to FIG. 9, an ultrasound is shown with device 200 inserted within the vagina and positioned about the cervix. Device 200 is shown as an echolucid structure positioned around the cervix and sleeve 202 and ring 240 are visible. This ultrasound shows an elongation of the cervical canal 118 after implantation of the present invention and resolution of amniotic membranes funneling.

The present invention stabilizes the relationship between cervix 109 and uterus 111 using the mechanical transmission of radial forces. In this manner, the present invention mechanically reinforces the cervical area of the uterus in order to stabilize, and/or to increase the longitudinal length of, the entire anatomical area, including the cervix. In normal circumstances the upright position of the patient results in greater hydrostatic pressure in the IOS and in a patient with cervical insufficiency, resulting in further cervical shortening. The present invention prevents the further shortening of the uterine cervical length when the patient is in an upright position. Such advantages serve to decrease the incidence of premature rupture of the membranes, one of the most common causes of premature babies. As such, the present invention is a new generation of cervico-vaginal pessary for the treatment of short cervices and cervico-isthmic insufficiency (also known as cervical incompetence).

Additionally, the present device stabilizes the cervix, elongates the cervical canal, decreases funneling and prevents further shortening of the cervix. These modifications of the cervical morphology are expected to be associated with decreased rates of preterm birth and its associated costs and complications.

Drug Eluting Applications

Figure 10:
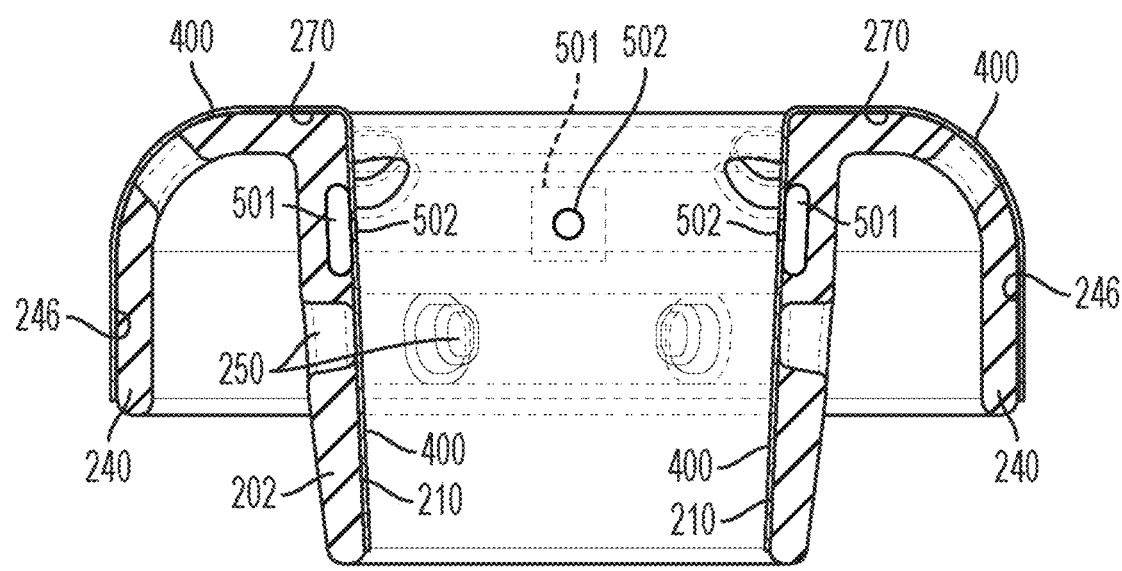
FIG. 10 is a view of an alternate embodiment the present invention.

Referring now to FIG. 10, an embodiment of the present invention is shown having a coating 400 applied to interior surface 210 of sleeve 202, superior surface 270 of annular member 226, and outer surface 246 of ring 240. While coating 400 is shown coating the interior surface 210 and surfaces 270 and 246, it may be preferable to only cover a portion of such surfaces, for example only interior surface 210 if the intent is to limit deliver of a medication or drug to cervix 109. Additionally, coating 400 may be located proximate apertures 250 which further serves to permit the drug or medication to easily transfer throughout device 200 and the vaginal and cervical region.

Coating 400 would typically comprise a drug eluting technology (a/k/a as "DE Technology" to one-skilled-in-the-art) for dispensing medication over a period of time for a specific application. For example, in the case of the present invention, a drug may be used in the coating which deliveries a predetermined amount over a given time to maintain the mother's cervical length and the homeostasis of the baby, such as the medication progesterone or prostaglandin inhibitors such as indomethacin. The eluting process may deliver drugs at a rate from 1 mg to 1000 mg daily. Progesterone is available, for example, from Ferring Pharmaceutical in Parsippany New Jersey Prostaglandin inhibitors such as indomethacin are available, for example, from G&W Laboratories, Inc. South Plainfield, NJ 07080

Typically, coating 400 is manufactured by mixing the medication with a polymer and applying it to the device 200 at the specified areas or throughout device 200. The coating is permitted to dry prior to installation in a patient.

Another alternative to the use of coating 400 is to impregnate the material used to manufacture the device with drug or medication to permit the medication to be released slowly over time. The medication may be mixed with the silicone or other gels or constituents used in preparing the source material at the time of manufacture of device 200.

Yet another alternative to the use of coating or impregnating the source material, may be to place the medication is a pellet or rod form within slots 501 of sleeve 202 of device 200 at the time of molding device 200 as shown in FIG. 10. Slots 501 are in fluid communication with the interior of sleeve 202 through ports 502 thereby allowing the medication to be in contact with the cervix.

Sensor Applications

As one skilled in the art realizes, parturition in mammals is preceded by two physiological phenomena: (1) increased excitability and (2) increased connectivity among the myometrial cells, changes which are reflected in an electrical myogram of the uterus. The uterus is a smooth muscle syncitium which contracts spontaneously and autonomously without the need for any neuronal control. It achieves this through the formation of gap junctions that interconnect the cells such that the action potentials propagate through the smooth muscle cells. The abnormal excitation of the uterus may be abolished with overriding currents in a similar fashion to other excitable tissues. Such physiological relationships permit the placement of various sensors to achieve preferred results as discussed below.

Figure 11A:
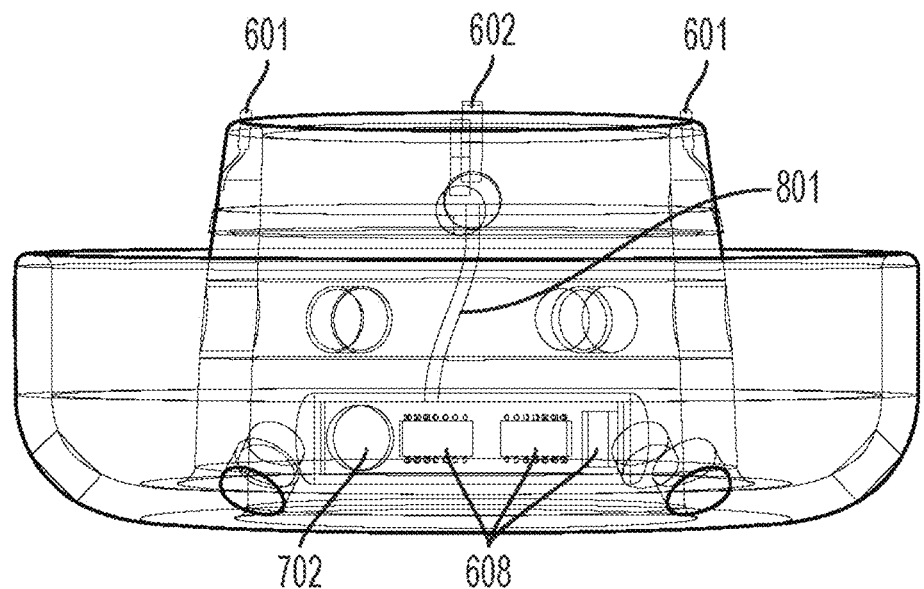
FIGS. 11A and 11B are views of yet another embodiment of the present invention.
Figure 11B:
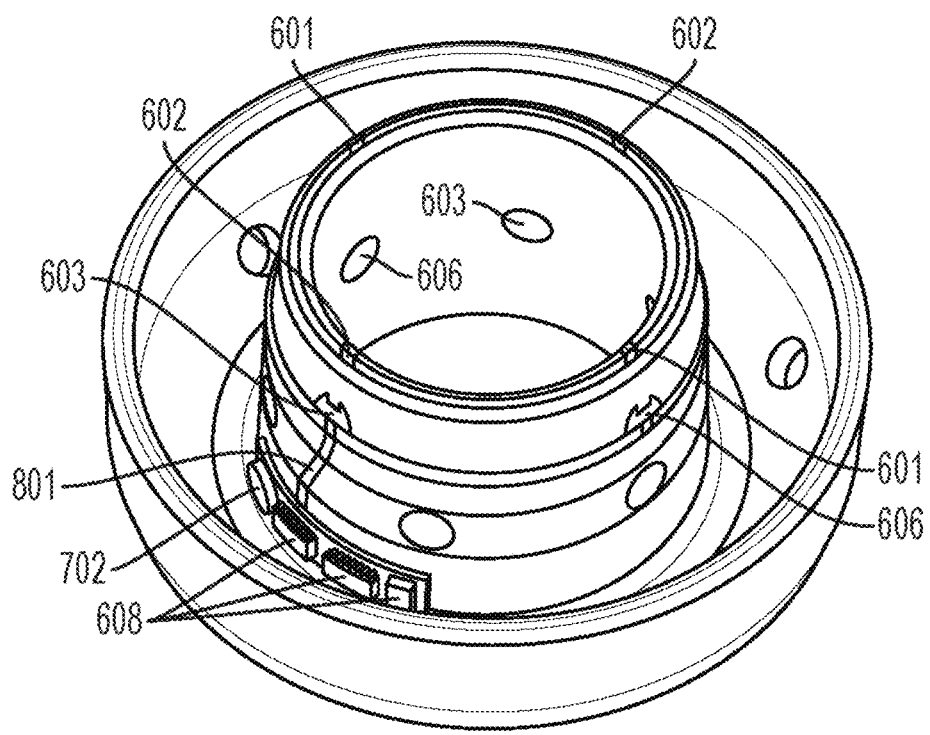
Figure 12:
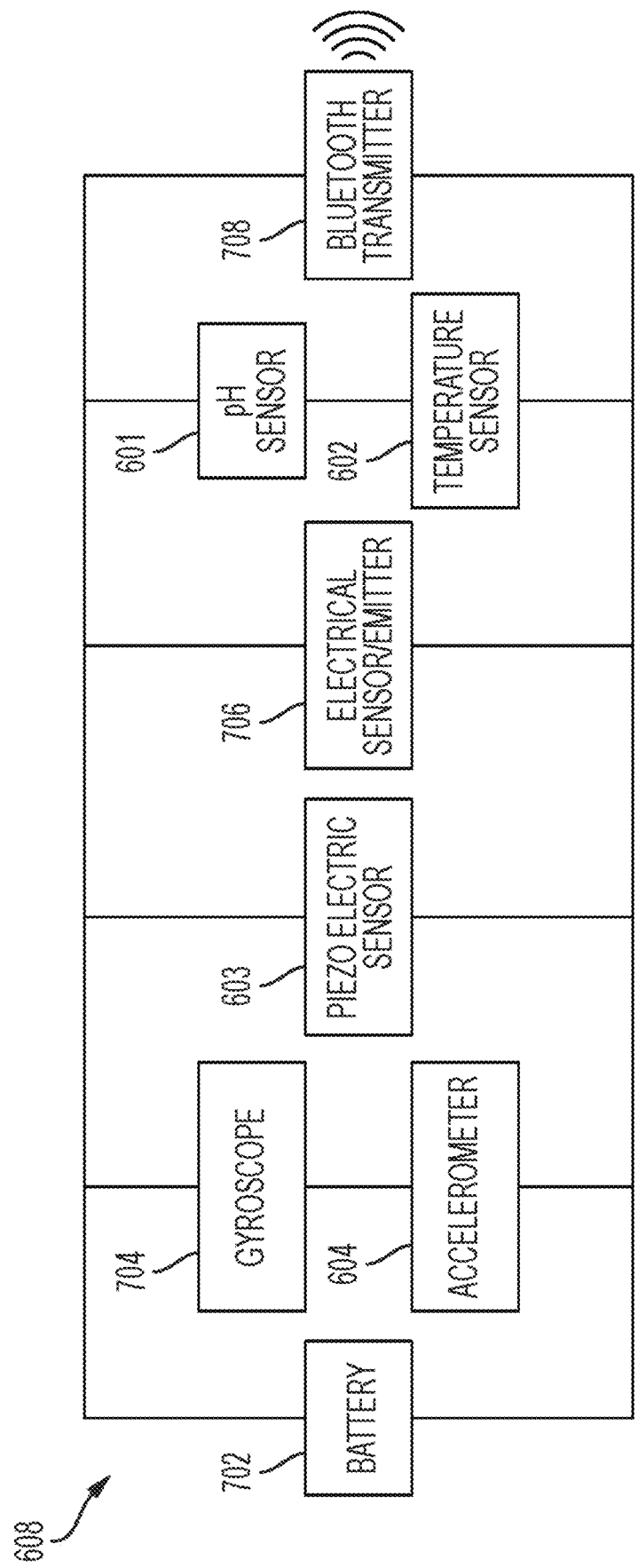
FIG. 12 is a schematic of the alternate embodiment of the present invention as shown in FIGS. 11A and 11B.

Referring now to FIGS. 11A, 11B and 12, an embodiment of the present invention is shown having various sensors which perform functions as described herein. Chemical meters 601 are positioned within the second edge 206 of sleeve 202. Meters 601 can capture change in the acidity or alkalinity of the cervix. The chemical receptors of meter 601 may detect pH changes that are transduced into voltages changes and then amplified using miniature transistors that transmit the voltage changes via Blue-tooth to a processing unit, such as an IOS device (iWatch or iPhone, for example) or Android based devices. There the signal can be further processed, for example, using a combination of filters, amplified and displayed as pH changes on a graphical user interface. An example of a suitable pH meter 601 is model LMP91200 available from Texas Instruments in Dallas, Texas http://www.ti.com/lit/ds/symlink/lmp91200.pdf Referring still to FIGS. 11A, 11B and 12, at least one temperature sensor 602 is embedded within member sleeve 202 to capture any change in the temperature of the cervix. Temperature changes are transduced into voltages changes that can be amplified using miniature transistors that transmit the voltage changes via Blue-tooth to a processing unit, such as an IOS device (iWatch or iPhone, for example) or Android based devices. There the signal can be further processed, for example, using a combination of filters, amplified and displayed as temperature changes on a graphical user interface. An example of a suitable temperature sensor 6012 is model 111-102CAJ-H01 available from Honeywell International in Charlotte, North Carolina haps:// sensing.honeywell.com/111-102CAJ-H01-thermistors Referring still to FIGS. 11A, 11B, and 12, at least one piezoelectric sensor 603 is embedded within member sleeve 202 to capture any change in stress strain in the cervix. Excitation of the uterus causes voltages changes which can be amplified using miniature transistors that will be transmitted via Blue-tooth to a processing unit, such as an IOS device (iWatch or iPhone, for example) or Android based devices where the signal can be further processed and displayed as contractions as a function of time. An example of a suitable piezoelectric sensor 603 is model RS Pro 632146 available from Allied Electronics Automation in Fort Worth, Texas https://www.alliedelec.com Referring still to FIGS. 11A, 11B and 12, at least one accelerometer 604 is also embedded within circuitry 608 attached to sleeve 202. Accelerometer 604 captures any change in movement or displacement of cervix 109. Such movement or displacement changes are transduced into voltages changes that can be amplified using miniature transistors that transmit the voltage changes via Blue-tooth to a processing unit, such as an IOS device (iWatch or iPhone, for example) or Android based devices. In this manner the movement or displacement changes can be monitored. To supplement the reading of accelerometer 604, a gyroscope 704 (see FIG. 12) may be included which operates in conjunction with the accelerometer 604 to generate an orientation signal of the patient. An example of a suitable accelerometer 604 and gyroscope 704 is model LSM303 available from Adafruit Industries of New York, New York haps://www.adafruit.com/product/1120

Referring still to FIGS. 11A, 11B and 12, at least one electric sensor and emitter 606 is shown having metallic unipolar and/or bipolar electrodes embedded within sleeve 202. Sensor/emitter 606 captures any changes in electrical currents. These currents are measured at the proximate level of the cervix in the form of electrical pulses or bursts which reflect increased electrical activity associated with a contraction and measured in millivolts. Once again, such electrical signals can be amplified using miniature transistors that transmit the voltage changes via Blue-tooth to a processing unit, such as an IOS device (iWatch or iPhone, for example) or Android based devices. Spectral and/or temporal parameters are handled with appropriate filters. In this manner, premature contractions may be measured. The physician may then, if desirable, attempt to stop the contraction by generating a signal from the processor back through the Blue-tooth connection to electrical circuitry 608 and, using battery 702, send a current to emitter 606 to interrupt the contraction. An example of a suitable sensor/ emitter 606 model UA741CP available from Texas Instruments in Dallas, Texas http://www.ti.com/lit/ds/symlink/ ua741.pdf With reference to FIG. 12, the electrical circuitry 608 is shown in schematic form having a battery 702 to power circuitry 608 and return a signal through meter 606 to attempt to interrupt a premature contraction. Circuitry 608 includes pH meter 601, temperature sensor 602, piezoelectric sensor 603, accelerometer 604, gyroscope 702, and voltage meter/emitter 606. Circuitry 608 also includes a Blue-tooth transmitter 708. The various sensors and meters may be connected within circuitry 608 by electrical connections or wires 801. In this manner, Blue-tooth transmitter 708 may communicate with a processing unit, such as an IOS device (iWatch or iPhone, for example) or Android based devices as described above, providing through a useful graphical interface, data helpful for the physician to evaluate the patient's condition and to evaluate the performance of the pessary device in preventing PTB. An example of a suitable Blue-tooth transmitter 708 is model TDK SESUB-PAN-D14580 available from TDK Corporation in Uniondale, New York https://product.tdk.com/en/search/rf/ rf/module/info?part_no=SESUB-PAN-D14580

Additional modifications of the present invention as shown in FIGS. 11A, 11B, and 12 allowing for the detection of electrical, chemical, positional and temperature signals from the cervix and uterus by the detection of movement, temperature, pH changes, position and uterine contractile activity will be apparent by those skilled in the art based on this disclosure without altering the inventive concepts and principles embodied therein. The embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

Manufacturing

As noted above, device 200 is preferably manufactured of a medical grade polymeric material, more preferentially a silicone or polyurethane with elastic properties that allows segmental compression of certain structures after implantation for maximum patient comfort. It should be inert and biologically compatible. Such medical gels are well known to those skilled in the art.

Device 200 may be manufactured from a mold created by a digital design using a 3D printer. The mold is then used to create a reverse casting for the final product, a process well known to those skilled-in-the-art. In this manner, device 200 may be manufactured as a unitary piece.

In order to provide the necessary pliable characteristics for ease of installation as discussed below, the thickness of sleeve 202 is between about 0.5 mm and about 5 mm, and preferably between about 0.8 mm and about 3 mm. Most preferably, sleeve 202 is about 2 mm in thickness.

Additionally, in order to provide the necessary pliable characteristics for ease of installation as discussed below, the thickness of annular member 226 is between about 0.5 mm and about 5 mm, and preferably between about 0.8 mm and about 3 mm. Most preferably, annular member 226 is about 2 mm in thickness.

Moreover, in order to provide the necessary pliable characteristics for ease of installation as discussed below, the thickness of ring 240 is between about 0.5 mm and about 5 mm, and preferably between about 0.8 mm and about 3 mm. Most preferably, ring 240 is about 2 mm in thickness.

In order to provide optimum hardness yet not inhibit pliability, the optimum hardness of device 200 is preferably between about 20 ShoreA and about 60 ShoreA, most preferably between about 30 ShoreA and about 50 ShoreA.

Patient Insertion

Figure 15:
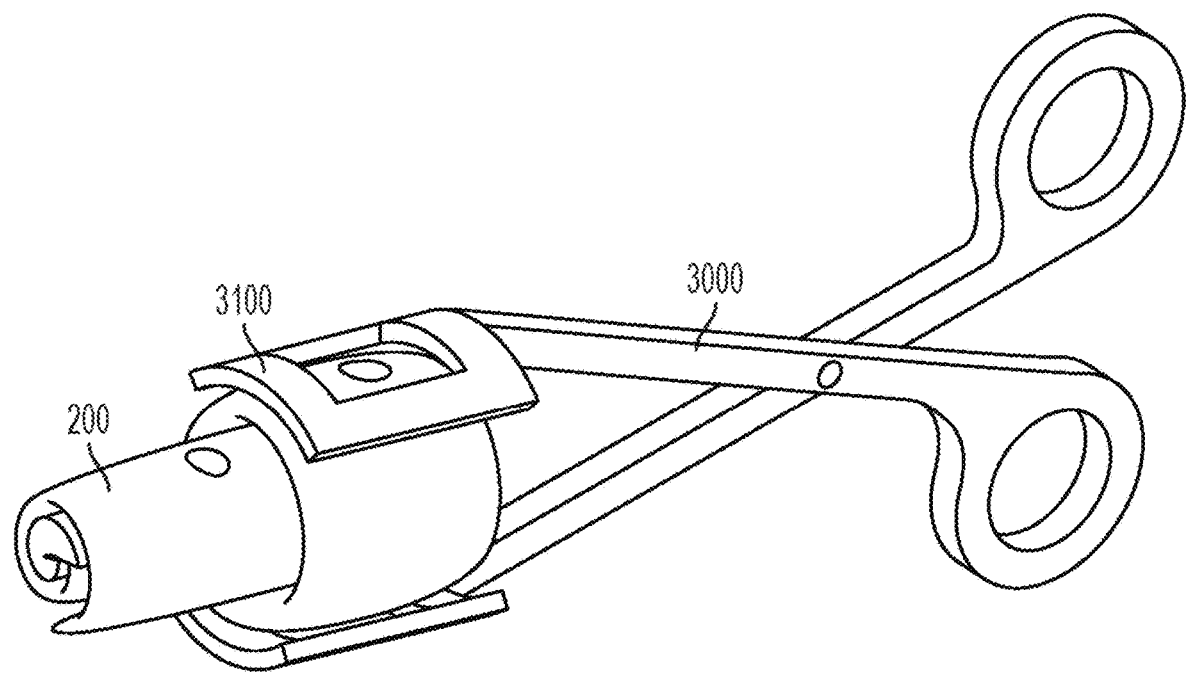
FIG. 15 is an isometric view of the present invention in a rolled configuration and being retained by curved forceps for insertion in a patient.
Figure 16:
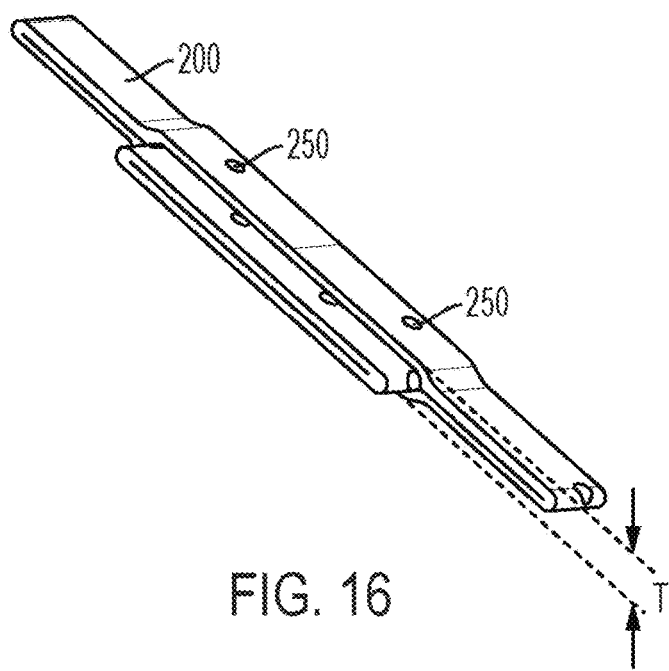
FIG. 16 is an isometric view of the present invention compressed flat as an alternative configuration prior to insertion in a patient.
Figure 17:
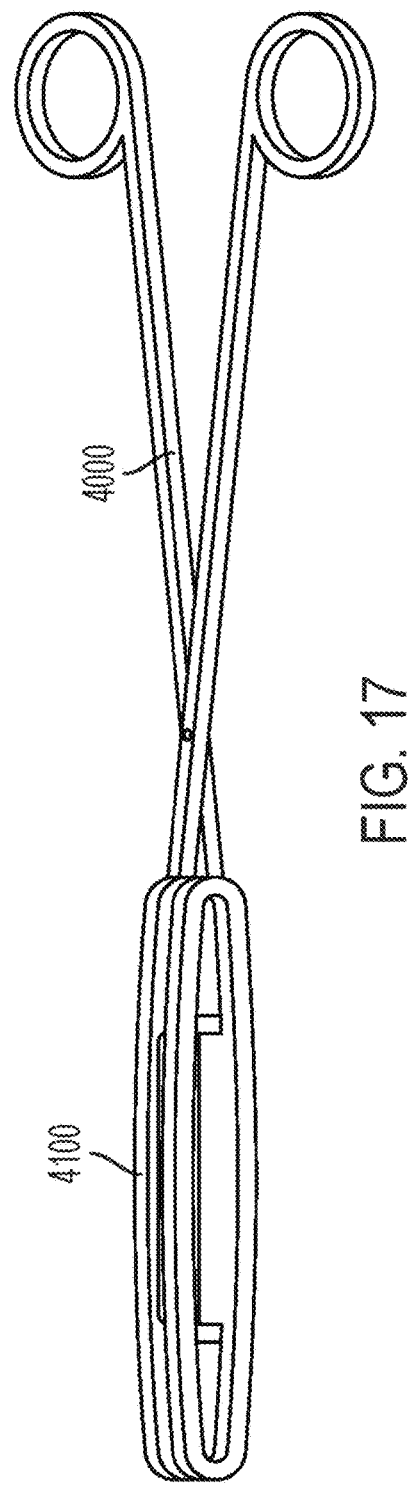
FIG. 17 is an isometric view of alternative forceps used to compress the present invention in the alternative configuration shown in FIG. 16.
Figure 18:
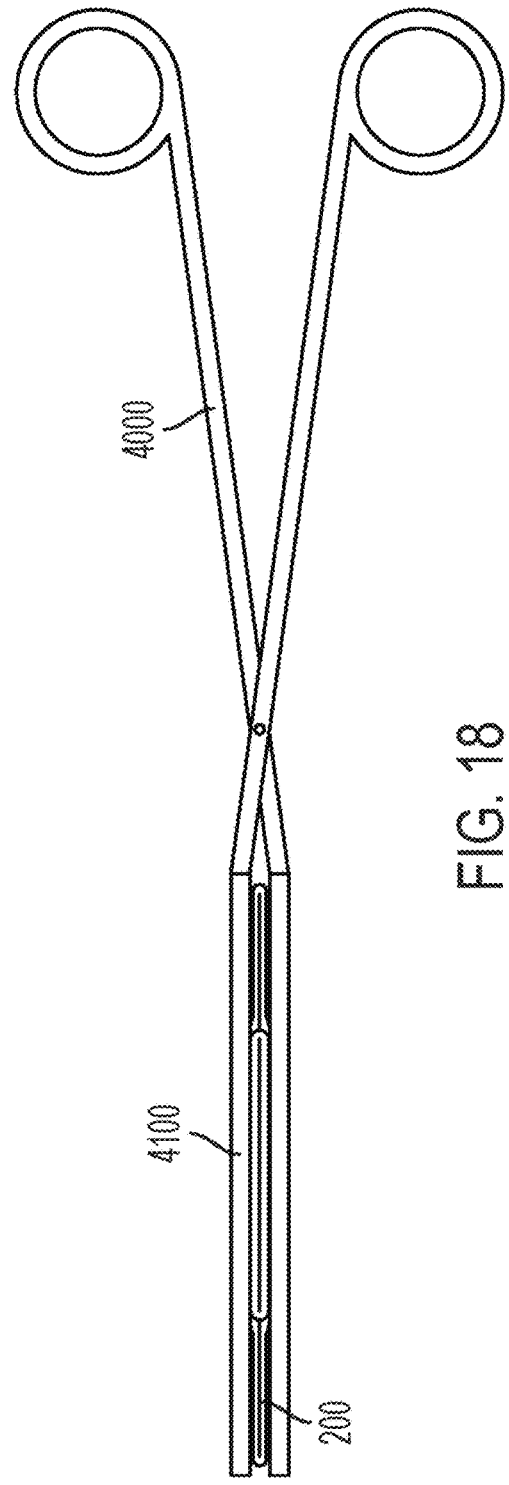
FIG. 18 is an isometric view of the present invention compressed in the alternative flat configuration of FIG. 16 by the alternative forceps shown in FIG. 17.

Referring to FIGS. 13-18, device 200 is shown is a circular configuration (FIGS. 13-14) or in a compressed or flattened configuration (FIG. 16). Referring to FIG. 15, forceps 3000 having curved forks 3100 are used to secure device 200 when in a circular configuration for patient insertion. Alternatively, FIGS. 17-18 show forceps 4000 used to secure device 200 as shown in a flattened configuration (See FIG. 16). Forceps forks 4100 (See FIGS. 17-18) retain the flattened device 200 in the configuration shown in FIG. 16 for patient insertion.

In order to comfortable insert device 200 into the vagina and onto the cervix, device 200 may be compressed longitudinally as shown in FIG. 16 to a thickness "T" of no more than between about 4 mm and about 15 mm, and more preferably no more than about 8 mm. Also, referring to FIGS. 13 and 14, device 200 may be collapsed circumferentially to a circular diameter no more than between about 5 mm and about 40 mm, and more preferably no more than 29 mm.

The placement of a device 200 is simple and straightforward. Unlike the placement of regular pessaries, the present invention does not require sizing. Customization of the device is, nevertheless, possible once the physician knows the characteristics of the cervix per transvaginal ultrasound.

Placement of device 200 is possible under direct visualization or by digital exam.

Figure 13:
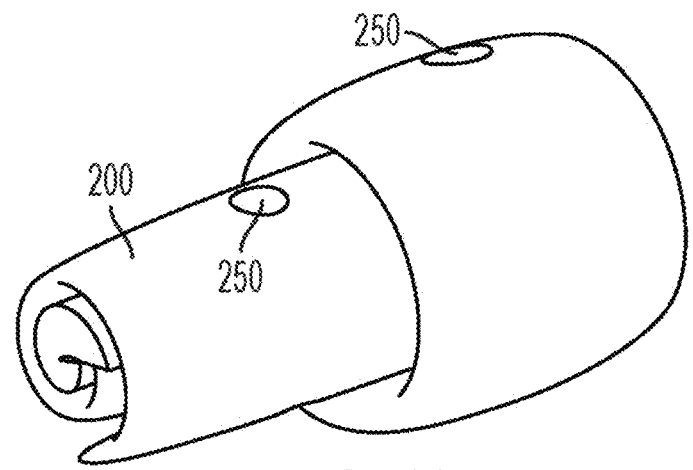
FIG. 13 is an isometric view of the present invention rolled prior to insertion in a patient.
Figure 14:
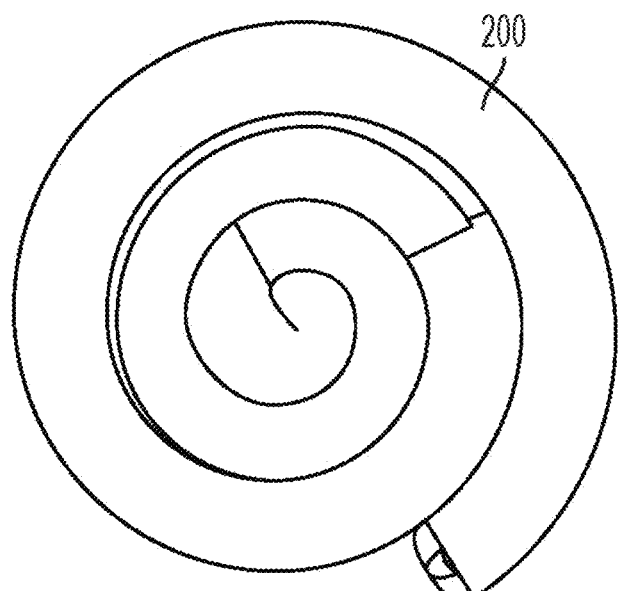
FIG. 14 is an end view of the present invention in a rolled configuration as shown in FIG. 13.

With respect to direct visualization, the following steps are preferably used in the placement of device 200 in the circular configuration shown in FIGS. 12-13 using direct visualization and forceps 3000 as shown in FIG. 15:

1. Have a chaperone.
2. Wear dry sterile gloves.
3. Place and secure a sterile speculum in the vagina to visualize the cervix.
4. Grasp device 200 using a ring forceps 3000, fold annular member 226 (bringing sides together) place ring 240 towards sleeve 202 and ring 240, bringing the sides together toward sleeve 202 and ring 240, resulting in the circular configuration shown in FIGS. 12-13.
5. Lubricate edge 228, ring 240, annular member 226, and surfaces 208 and 210 of sleeve 202 with a water-soluble lubricant.
6. Compress device 200 at the annular member 226 holding sleeve 202 toward the exterior.
7. Advance device 202 past the introitus with the dominant hand and allow device 202 to open into its final shape after passing the introitus.
8. Use the forceps 3000 guide device 202 past the cervix by gently push on the inner portion of annular member 226 advancing sleeve 202 around the cervix into the position shown in FIG. 8A.
9. Verify that the external OS is contained within sleeve 202 above at least the second edge 206 of sleeve 202.
10. While holding device 200 in place with the forceps 3000, unlock the speculum and start removing it while carefully observing final placement of device 200.
11. Remove the speculum.
12. After speculum removal ask the patient if she feels a foreign body. She should not.
13. May be helpful to get a transvaginal measurement of the cervical length at this time.

The following steps are preferably used in the placement of the present invention during a digital examination:

1. Have a chaperone.
2. Wear dry sterile gloves.
3. Lubricate surfaces 205 and 210 of sleeve 202 and surface 246 of ring 240 with a water-soluble lubricant.
4. Compress device 200 at the annular member 226 holding sleeve 202 toward the exterior.
5. Use one finger of the opposite hand to slightly depress the perineum.
6. Hold device 200 substantially parallel with the introitus.
7. Direct edge 228 past the introitus and allow device 200 to open into its final shape after passing the introitus.
8. Use the index and middle fingers to guide annular member 226 along the posterior vaginal wall into the posterior fornix until it does not advance any further.
9. Then use the index and middle fingers to guide the annular member 226 along the anterior vaginal wall into the anterior fornix until it does not advance any further thereby having placed sleeve 202 around the cervix into the position shown in FIG. 8A.
10. Verify that the external OS is contained within the sleeve 202 above at least the second edge 206 of sleeve 202.
11. Ask the patient if she feels a foreign body. She should not.
12. You may want to get a transvaginal measurement of the cervical length at this time.

Due to the snug retention of the cervix within sleeve 202, device 200 also serves to further wedge the patient's cervix within sleeve 202 when the patient is standing. The weight of the pregnant uterus onto the cervix and in turn device 200 may prevent premature dilatation of the cervix and premature rupture of the membranes. Furthermore, device 200 blocks the fetal head from descending and pressing on the internal ostium. This is a further advantage of device 200 in retaining the fetus and preventing PTB.

The device 200 described in the various embodiments herein may be powered and/or one or more energy storage units thereof charged by receiving wireless power from a master device. In some embodiments, the device 200 may also or alternatively transmit power through a wireless power transceiving structure. References here in to "powering" the pessary may refer to either directly powering the device from wireless transmissions or powering the device from an energy storage device that is charged from the wireless transmissions. Wireless power may improve the safety and/or comfort of the device 200 by allowing use in a patient of the device 200 with a smaller battery or no battery or other energy storage device. Wireless power reception by the device 200 may be supported by wire structures attached to, integrated with, or otherwise in electrical communication with the device 200. The attachments may be, for example, affixed to a surface of the structure or embedded into a portion of the structure of device 200. Examples of power transceiving structures usable with the pessary device 200 may include wires, conductive planes, and/or printed circuit traces, but the power transceiving structure may be any structure that is configured to respond, resonate, be excited by, or react to radio frequency (RF) energy provided by a corresponding power transmission structure in a master device. The power transceiving structures may be configured to receive the power by a combination of size, shape, and/or orientation on the pessary.

Figure 19:
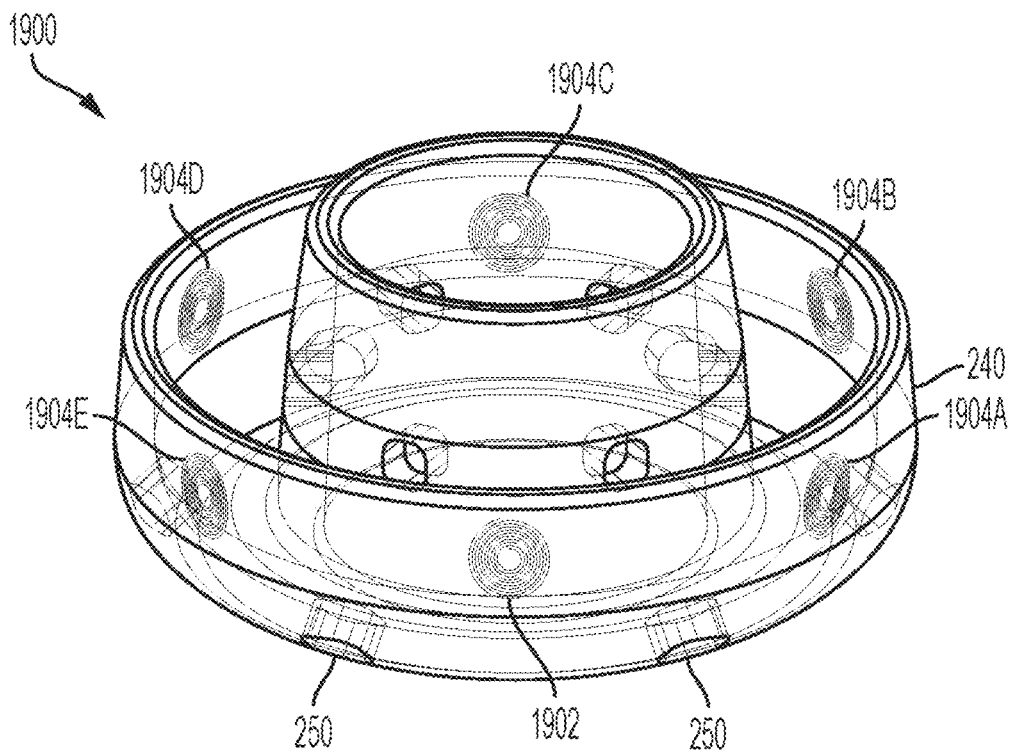
FIG. 19 is an isometric view of the inferior side of the present invention with power transceiving structures on portions of the pessary for wireless power reception according to some embodiments of the disclosure.
Figure 20:
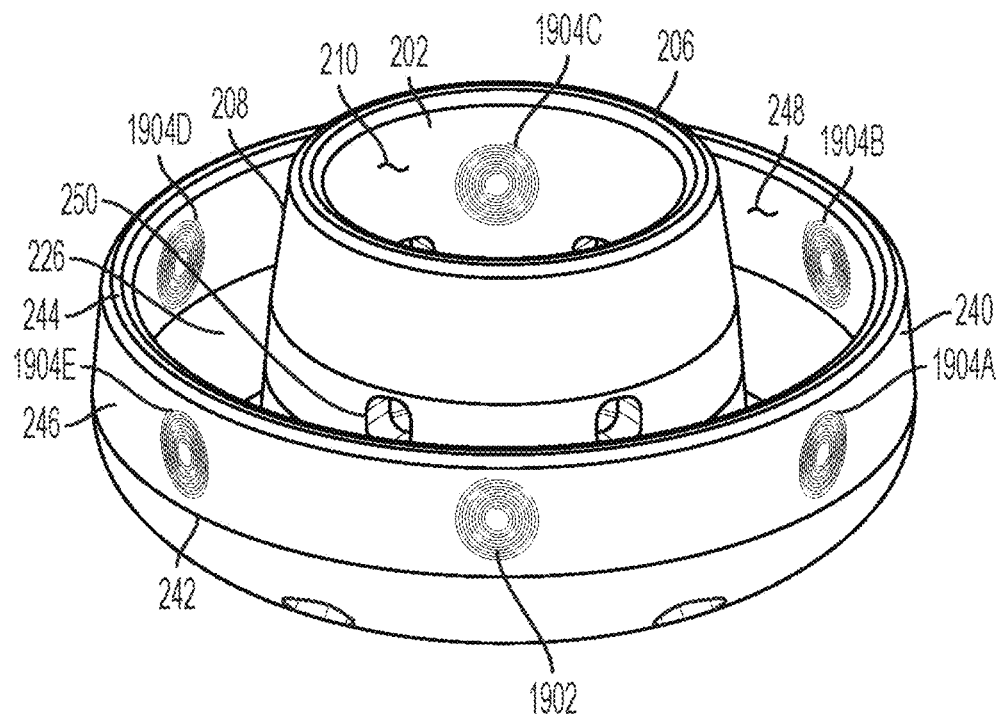
FIG. 20 is another isometric view of the inferior side of the present invention with power transceiving structures on portions of the pessary for wireless power reception according to some embodiments of the disclosure.

One example of a power transceiving structure for the device 200 to support wireless power reception is shown in FIGS. 19-20 as device 1900. Device 1900 may be any of the embodiments described above with reference to device 200 with a power transceiving structure. FIG. 19 shows the inferior view of device 1900, and FIG. 20 is an inferior view of device 1900. Elements of the present invention are shown with similar numerals to reflect the same elements as discussed above. A device 1900 includes an arrangement for a pessary device including apertures 250, sleeve 202 with first edge 204, second edge 206, outer surface 208, and interior surface 210, ring 240 with first edge 242, second edge 244, outer surface 246, and inner surface 248, and an annular member or portion 226 having an outer edge 228 and an inner edge 230. The device 1900 may include other combinations of features described above with respect to device 200.

For wireless power reception, the device 1900 includes a first power transceiving structure 1902 arranged as a spiral of wire forming a plurality of series-coupled concentric circles. The power transceiving structure 1902 spans an area of a portion of the device 1900, such as a portion of the ring 240 as shown, or in other embodiments may span an area of a portion of the device 1900 in the annular member 226 and/or the sleeve 202. Additional power transceiving structures 1904A-E may be included in the device 1900 to improve wireless power reception. The power transceiving structures 1902 and 1904A-E may be arranged in a manner to facilitate collapsing of the device 1900 to allow insertion of the device 1900 as shown and described with reference to FIGS. 13-18. For example, the size of the structures 1902 and 1904A-E may be small enough and/or the locations selected such that the collapsing and/or expanding of the device 1900 does not short circuit or otherwise break the structures 1902 and 1904A-E. The various structures 1902 and 1904A-E may be coupled together in series or in parallel depending on a power output level desired for powering the electrical circuitry. Alternatively, the various structures 1902 and 1904A-E may be individually coupled to a power controller with additional circuitry configured to condition and combine power received from the various structures to obtain a desired voltage level and power level. The structures 1902 and 1904A-E may be distributed asymmetrically around the circumference to facilitate the collapsing and/or expanding of the device in any direction.

Each of the power transceiving structures 1902 and 1904A-E may have a number of loops selected to obtain a desired level of inductance coupling with a transmitter, such as between 2 and 20 loops, between 5 and 15 loops, or between 8 and 12 loops. In some embodiments, the power transfer may occur through radio frequency (RF) electromagnetic waves in the 50 Hz to 3 GHz range, or more particularly in the 900-999 MHz range, and have a power transfer of 1-10 Watts. The received power may be used to charge a battery, capacitor, or other energy storage device in the device 1900 from which the device 1900 is powered or may be used to directly power electrical circuitry in the device 1900. In some embodiments, data transfer may occur over these RF electromagnetic waves, such as signaling an identifier (ID) or power transmission capability of the device 1900. Other data, such as sensor data, may also be transmitted through the wireless power coupling. For example, the pessary device may signal its model number of other identifier to the master device during initialization of wireless power transfer so that the master device may confirm that the received device is a pessary device and not another wireless device such as a mobile phone. As another example, the pessary device may have a unique certificate or other authentication data to allow only authorized master devices to transfer power to the pessary device and/or receive sensor data from the pessary device. Such authentication may prevent unauthorized individuals from accessing a patient's medical data that would otherwise be a violation of medical privacy laws.

Each of the wireless structures 1902 and 1904A-E may receive variable amounts of power from a transmitter based on the orientation of the wireless structures 1902 and 1904A-E relative to a transmitter that affects the level of power transfer from a master device. The inclusion of multiple power transceiving structures 1902 and 1904A-E improves wireless power transfer under different circumstances that change the orientation of the device 1900 relative to the transmitter. For example, a patient's facing towards or facing away from the transmitter may change the ratio of coupling with the transmitter between each of the power transceiving structures 1902 and 1904A-E in a different manner. The power transceiving structures 1902 and 1904A-E may each have different orientations with respect to each other and the device 1900 such that a coupling ratio of one of the wireless structures increase as a coupling ratio of another one of the wireless structures decreases. Thus, the power transceiving structures 1902 and 1904A-E may be configured to provide an approximately constant power level and/or a power level that remains approximately above a threshold power level required to operate the electronic circuitry of the device 200. In one example embodiment, the power transceiving structures 1902 and 1904A-E may be approximately equally spaced around a circumference of the ring 240. The power transceiving structures 1902 and 1904A-E may be embedded within the ring 240, such as between the inner surface 248 and outer surface 246. Some or all of the power transceiving structures 1902 and 1904A-E may alternatively be affixed to the inner surface 248 or affixed to the outer surface 246. Some or all of the power transceiving structures 1902 and 1904A-E may alternatively be embedded within the annular member 226 or the sleeve 202 or affixed to the outer edge 228 or the inner edge 230 of the annular member 226 or affixed to the outer surface 208 or the interior surface 210 of the sleeve 202.

Figure 21:
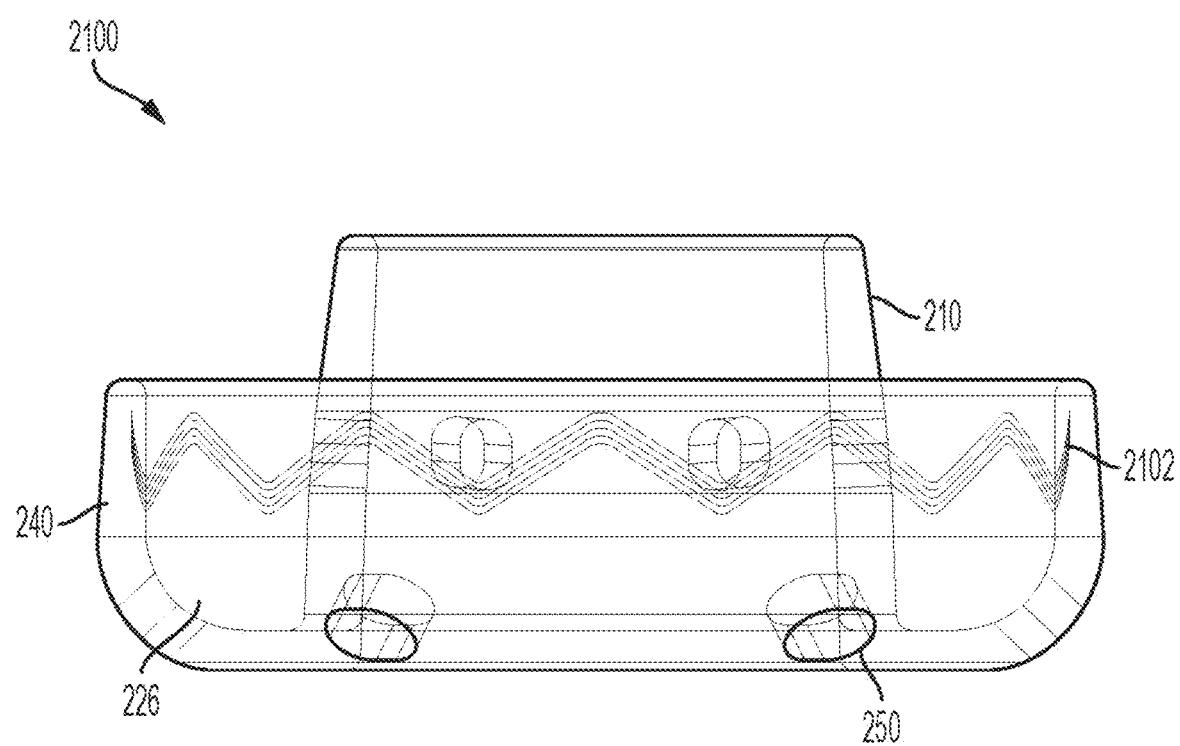
FIG. 21 is a side view of the present invention with power transceiving structures around a circumference of a portion of the pessary for wireless power reception according to some embodiments of the disclosure.
Figure 22:
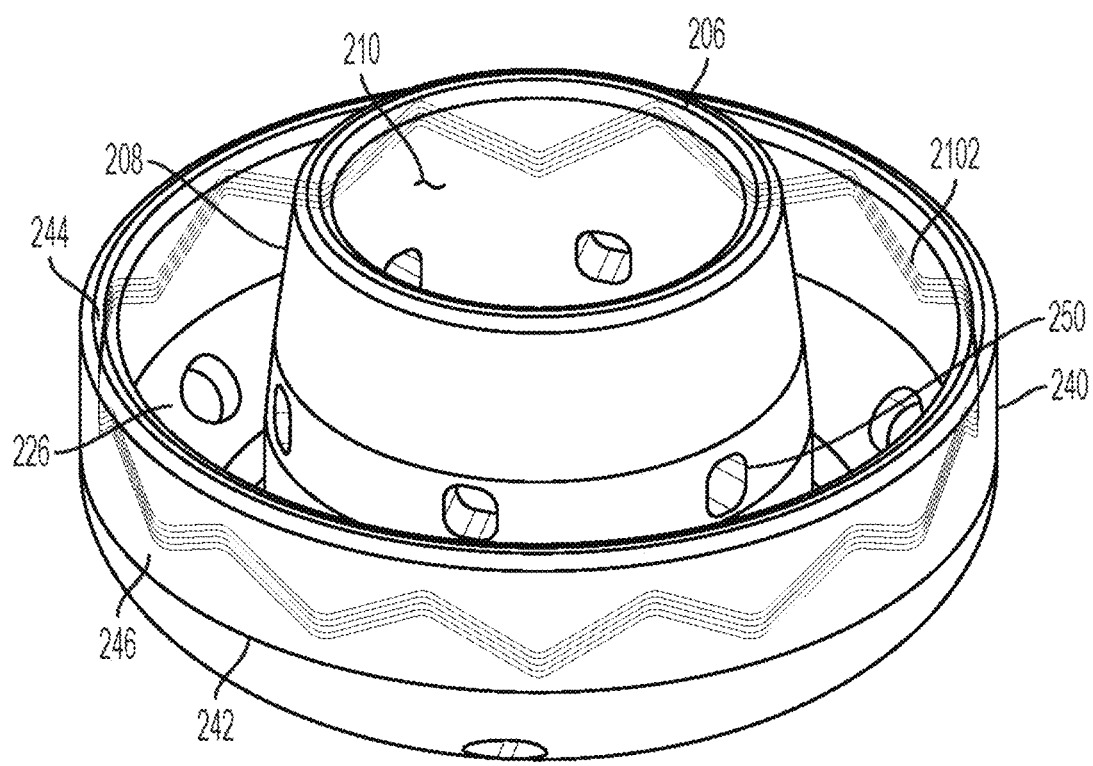
FIG. 22 is an isometric view of the inferior side of the present invention with power transceiving structures around a circumference of a portion of the pessary for wireless power reception according to some embodiments of the disclosure.

In some embodiments, one or more power transceiving structures may be wrapped around a circumference of portions of the device 200. One example of a power transceiving structure for the device 200 to support wireless power reception using power transceiving structures positioned around a circumference of the device 200 is shown in FIGS. 21-22. FIG. 21 shows the side view of device 2100, and FIG. 22 is another inferior view of device 2100. Elements of the present invention are shown with similar numerals to reflect the same elements as discussed above. Device 2100 includes a power transceiving structure 2102 with a wire of a radial pattern oriented around a circumference of a portion of the device 2100. The power transceiving structure 2102 may repeat multiple times around the circumference to form multiple substantially parallel loops. For example, power transceiving structure 2102 may be embedded within the ring 240, such as between the inner surface 248 and outer surface 246 of the ring 240. Some or all of the power transceiving structure 2102 may alternatively be affixed to the inner surface 248 or affixed to the outer surface 246 of the ring 240. Some or all of the power transceiving structure 2102 may alternatively be embedded within the annular member 226 or the sleeve 202 or affixed to the outer edge 228 or the inner edge 230 of the annular member 226 or affixed to the outer surface 208 or the interior surface 210 of the sleeve 202. The power transceiving structure 2102 may include a number of loops of wire stacked on each other with some separation between the loops along an axis extending through the sleeve 202 along an insertion direction. The power transceiving structure 2102 may have a number of loops selected to obtain a desired level of inductive coupling with a transmitter of a master device. In some embodiments, the power transfer may occur through radio frequency (RF) electromagnetic waves in the 50 Hz to 3 GHz range, or more particularly in the 900-999 MHz range, with a resulting power transfer of 1-10 Watts. The received power may be used to charge a battery, capacitor, or other energy storage device in the device 2100 from which the device 2100 is powered or may be used to directly power electrical circuitry in the device 2100. In some embodiments, data transfer may occur over these RF electromagnetic waves, such as signaling an identifier (ID) or power transmission capability of the device 2100. Other data, such as sensor data, may also be transmitted through the wireless power coupling. For example, the pessary device may signal its model number of other identifier to the master device during initialization of wireless power transfer so that the master device may confirm that the received device is a pessary device and not another wireless device such as a mobile phone. As another example, the pessary device may have a unique certificate or other authentication data to allow only authorized master devices to transfer power to the pessary device and/or receive sensor data from the pessary device. Such authentication may prevent unauthorized individuals from accessing a patient's medical data that would otherwise be a violation of medical privacy laws.

The power transceiving structure 2102 may be arranged in a manner to facilitate collapsing and/or expanding of the device 2100 to allow insertion of the device 2100 as shown and described with reference to FIGS. 13-18. For example, the power transceiving structure 2102 may have an alternating pattern of different angles at various turns at turning points around the circumference to reduce stress on the power transceiving structure 2102 when collapsing the device 2100. At each of the turns, the first power transceiving structure 2102 changes direction from oriented towards a first side of the pessary to oriented towards a second, opposite side of the pessary. In different embodiments, the power transceiving structure 2102 comprises segments alternating between +10 degrees and −10 degrees zig-zags from a circle drawn around the circumference of one portion of the device 2100. Alternatively, the segments may alternate between +15 degrees and −15 degrees, alternate between +20 degrees and −20 degrees, alternate between +30 degrees and −30 degrees, alternate between +40 degrees and −40 degrees, and/or alternate between +50 degrees and −50 degrees. In further embodiments, the power transceiving structure 2102 may comprise another alternating structure, such as a wave structure, similar to a sine wave, in which the change in curvature of the power transceiving structure 2102 is smooth around the circumference of the device 2100. Although some example angles are provided, the power transceiving structure 2102 may have segments with intersecting angles of any value between 1 degree to 179 degrees from a vertical plane, and more specifically 45 to 155 degrees from the vertical plane in some embodiments. The angles of the zigzag of each loop of the power transceiving structure 2102 may be symmetrical, but in some embodiments may vary from one loop to the next loop. The zig-zag shape of the circumferential coil power transceiving structure 2502 may facilitate the collapsing and/or expanding during insertion into the vagina.

Figure 23:
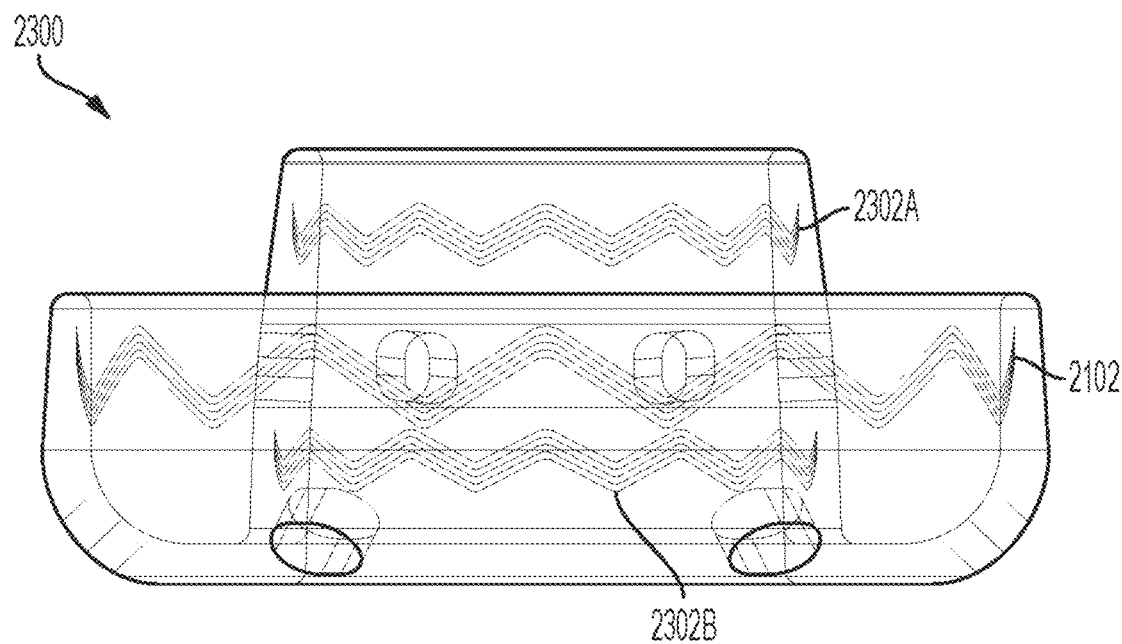
FIG. 23 is a side view of the present invention with power transceiving structures around a circumference of a portion of the pessary for wireless power reception according to some embodiments of the disclosure.
Figure 24:
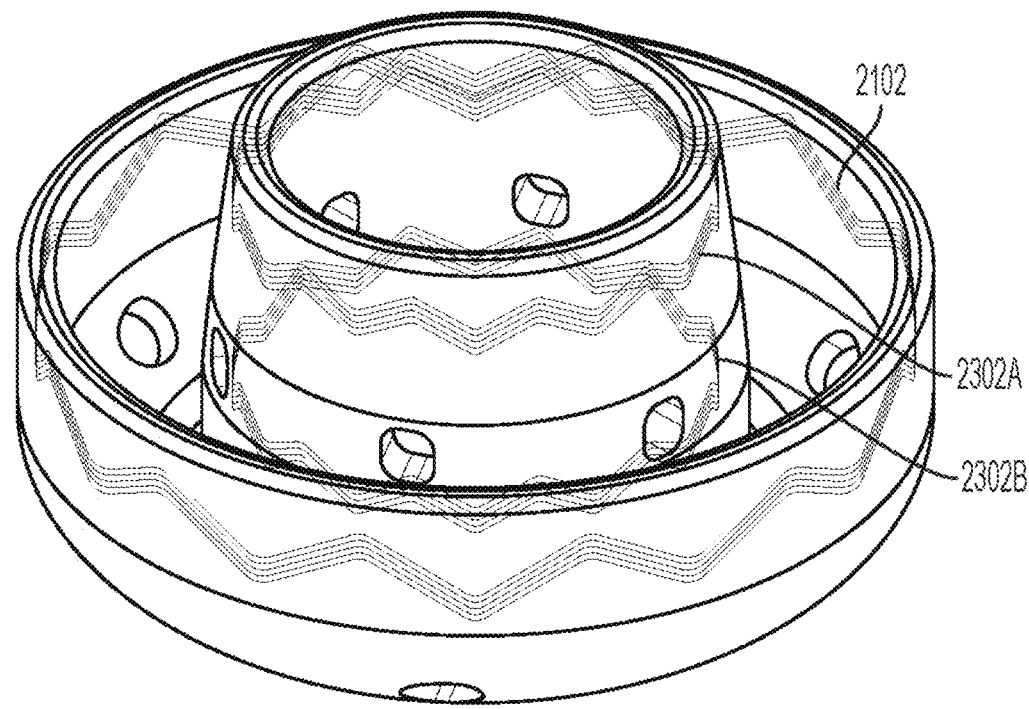
FIG. 24 is an isometric view of the inferior side of the present invention with power transceiving structures around a circumference of a portion of the pessary for wireless power reception according to some embodiments of the disclosure.

Multiple power transceiving structures such as the power transceiving structure 2102 shown in FIGS. 21-22 may be incorporated into a device to increase the amount of power transferred and/or to increase the reliability of the power transferred to the device 2100. For example, each of multiple power transceiving structures may be configured to couple to different wireless power transmitter configurations to support different master devices. Multiple circumferential power transceiving structures are shown in embodiments illustrated in FIGS. 23-24. A device 2300 may be any of the embodiments described above with regard to device 2100, but include multiple power transceiving structures. FIG. 23 shows the side view of device 2300, and FIG. 24 is another inferior view of device 2300. Elements of the present invention are shown with similar numerals to reflect the same elements as discussed above. The device 2300 includes the power transceiving structure 2102 and additional power transceiving structures 2302A-B.

Figure 25:
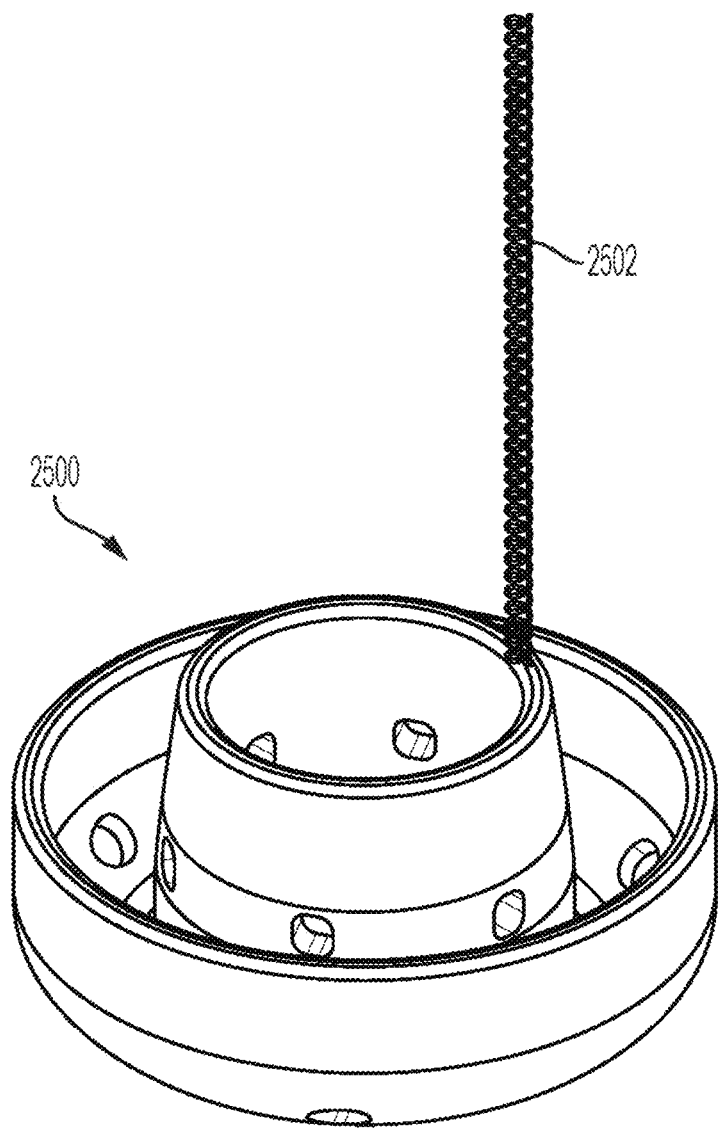
FIG. 25 is an isometric view of the inferior side of the present invention with a power transceiving structure of a hanging coiled wire for wireless power reception according to some embodiments of the disclosure.

In some embodiments, power transceiving structures may extend from the device 200. One example of a power transceiving structure for the device 200 to support wireless power reception using power transceiving structures positioned around a circumference of the device 200 is shown in FIG. 25. FIG. 25 shows another inferior view of device 2500, which may be any of the embodiments described above for device 200 modified to include power transceiving structures extending from the device 200. Elements of the present invention are shown with similar numerals to reflect the same elements as discussed above. A power transceiving structure 2502 may be coupled to the sleeve 202, and may be a coiled wire that resembles a spring that allows some compression of the power transceiving structure 2502 on an axis oriented along a long dimension of the power transceiving structure 2502. In some embodiments, the structure 2502 may be sheathed with a flexible membrane to provide a cylindrical housing for improving hygienic characteristics of the structure 2502. The power transceiving structure 2502 may be coupled at one of or between the first and second edges 204 and 206 of sleeve 202 or at or between other structures labeled and described with reference to FIG. 2. Alternatively, the power transceiving structure 2502 may be coupled to the ring 240, such as at or between the inner surface 248 and outer surface 246. The power transceiving structure 2502 may alternatively be affixed to the annular member 226 at or between the outer edge 228 or the inner edge 23 or affixed to the sleeve 202 at the outer surface 208 or the interior surface 210.

Figure 26:
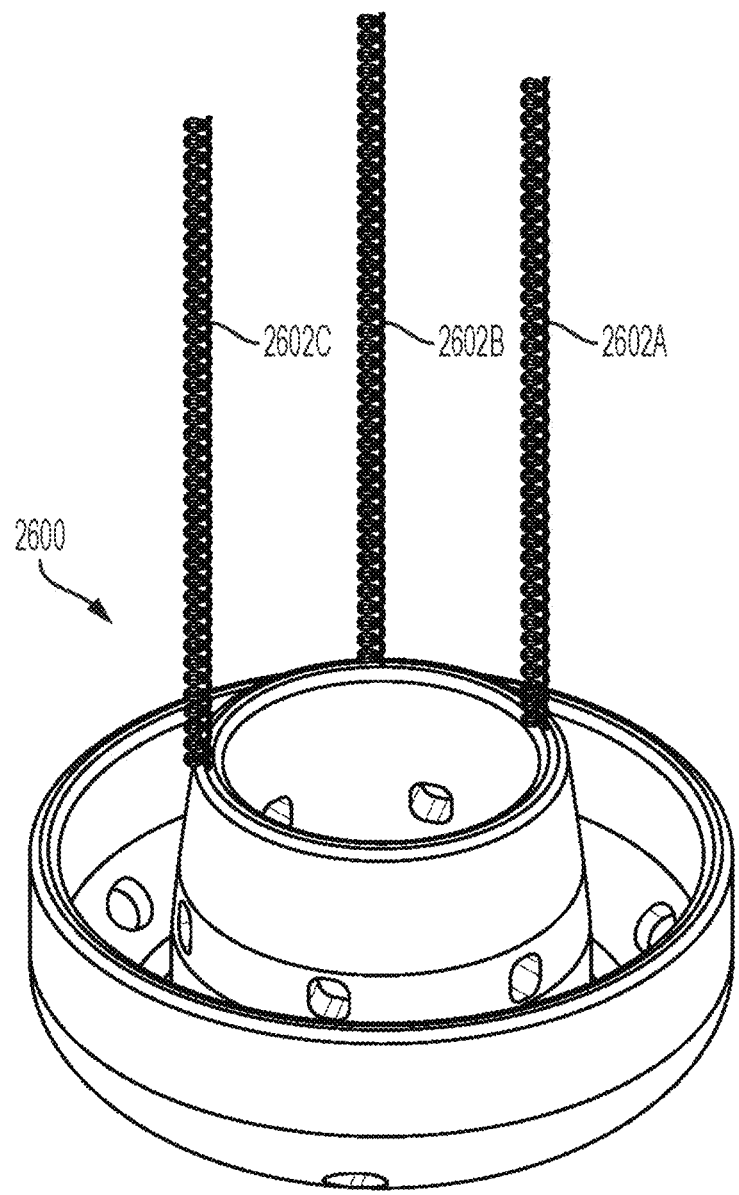
FIG. 26 is an isometric view of the inferior side of the present invention with power transceiving structures of hanging coiled wires for wireless power reception according to some embodiments of the disclosure.

Multiple power transceiving structures such as the power transceiving structure 2502 shown in FIG. 25 may be incorporated into a device to increase the amount of power transferred and/or to increase the reliability of the power transferred to the device 2500. FIG. 26 shows a device 2600 with multiple power transceiving structures 2602A-C. Each of these power transceiving structures 2502 and 2602A-C may have a different or same coiling configuration, such as different radius of curvature, length of coil, number of coils, and/or material. In some embodiments, the length of one or more of the power transceiving structures 2502 and 2602A-C may extend outside the patient to improve wireless power reception and/or wireless communications. The power transceiving structure 2102 may have a configuration selected to obtain a desired level of inductive coupling with a transmitter. In some embodiments, the power transfer may occur through radio frequency (RF) electromagnetic waves in the 50 Hz to 3 GHz range, or more particularly in the 900-999 MHz range, with a resulting power transfer of 1-10 Watts. In some embodiments, data transfer may occur over these RF electromagnetic waves, such as signaling an identifier (ID) or power transmission capability of the device 2600. Other data, such as sensor data, may also be transmitted through the wireless power coupling. For example, the pessary device may signal its model number of other identifier to the master device during initialization of wireless power transfer so that the master device may confirm that the received device is a pessary device and not another wireless device such as a mobile phone. As another example, the pessary device may have a unique certificate or other authentication data to allow only authorized master devices to transfer power to the pessary device and/or receive sensor data from the pessary device. Such authentication may prevent unauthorized individuals from accessing a patient's medical data that would otherwise be a violation of medical privacy laws.

Figure 27:
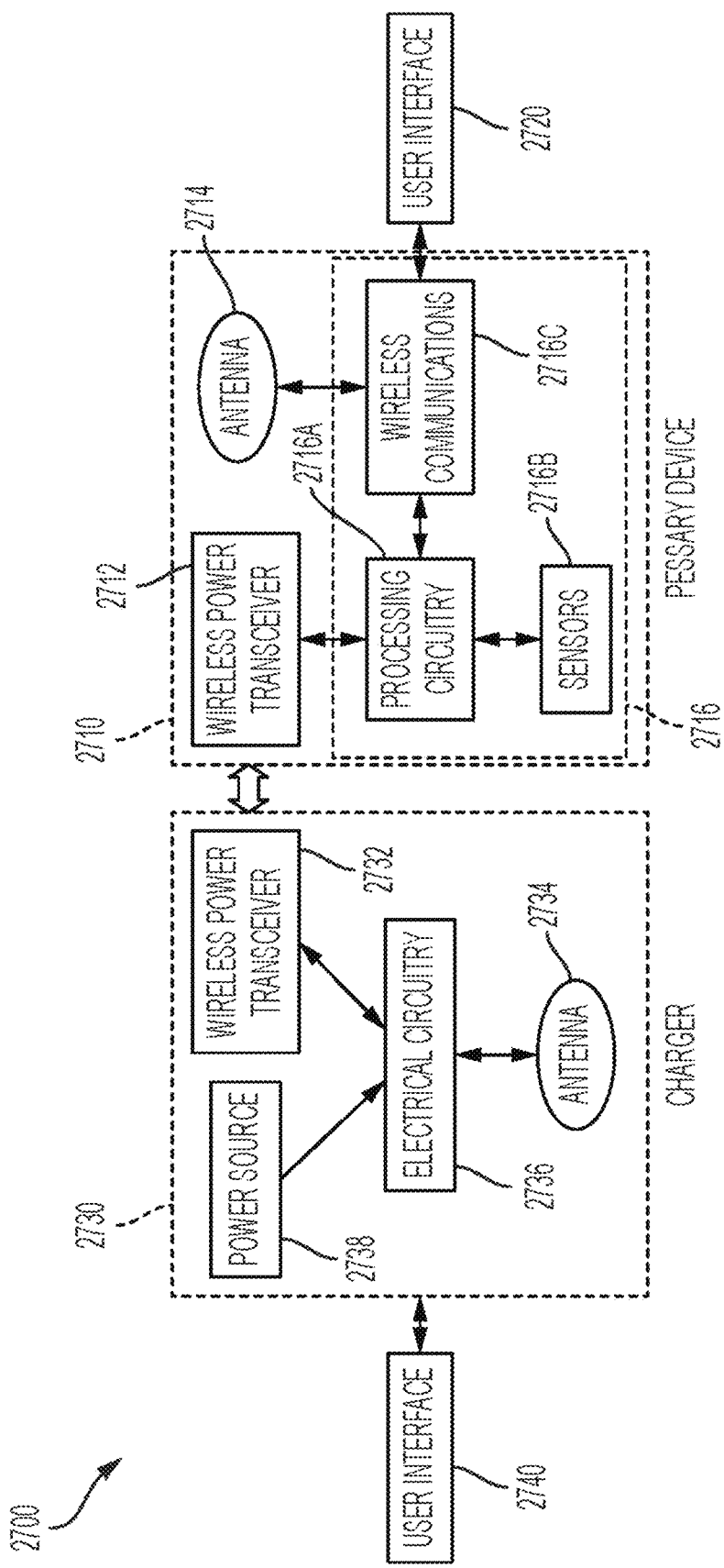
FIG. 27 is a block diagram illustrating a system for powering a pessary device of the present invention according to some embodiments of the disclosure.

A system 2700 supporting wireless power transfer to one of the devices described above is shown in the block diagram of FIG. 27. Any of the embodiments of the pessary device described herein may be used as pessary device 2710. The pessary device 2710 may include a wireless power receiver module 2712, which may include one of the power transceiving structures described herein, such as in the examples of FIGS. 19-26 or a combination of the examples of FIGS. 19-26, along with accompanying electronic circuitry, such as radio frequency (RF)-to-direct current (DC) and alternating current (AC)-to-DC converters, an energy storage device such as a battery or capacitor, and/or power conditioning circuitry. Wireless power received by the wireless power receiver module 2712 may be conditioned and used to power electronic circuitry 2716, including one or more sensors 2716B and processing circuitry 2716A for interfacing with the sensors 2716B. The processing circuitry 2716A may include, for example, signal processing circuitry, memory, filters, diodes, transmitters, wireless communication processing circuitry, such as for Bluetooth or other short- to medium-range communications and/or amplifiers. The received power may also power a wireless communications module 2716C for transferring data from the sensors 2716B to a remote device through antenna 2714. In some embodiments, the device 2710 may provide a user interface 2720 for allowing a user to retrieve and/or interact with data captured by the sensors 2716B.

The pessary device 2710 may inductively couple wireless power receiver 2712 to a wireless power transmitter 2732 of a master device 2730. The master device 2730 may also include a power source 2738, such as a battery or a wall alternating current (AC) power adapter. The power source 2738 provides power for wireless power transmission to the pessary device 2710 through the wireless power transmitter 2732 and for the electrical circuitry 2738. The wireless power transmitter 2732 may include a radio frequency (RF) generator and an inductive coil or other radiative element for generating electromagnetic (EM) waves for transmitting power to the wireless power receiver 2712. The master device 2730 may also include electrical circuitry 2736, which may include, for example, data processing circuitry and wireless communication circuitry. The electrical circuitry 2736 may be coupled to antenna 2734 for communicating with the pessary device 2710 to obtain data, such as measurement data from sensors 2716B. The master device 2730 may also provide a user interface 2740 for a user to receive status updates regarding the pessary device 2710, retrieve and interact with data from the pessary device 2710, and issue instructions to the pessary device 2710. In some embodiments, the user interface 2740 and/or 2710 may include a web page for interacting with the data and/or support for a data transfer protocol, such as the file transfer protocol (FTP), to download data files.

Figure 28:
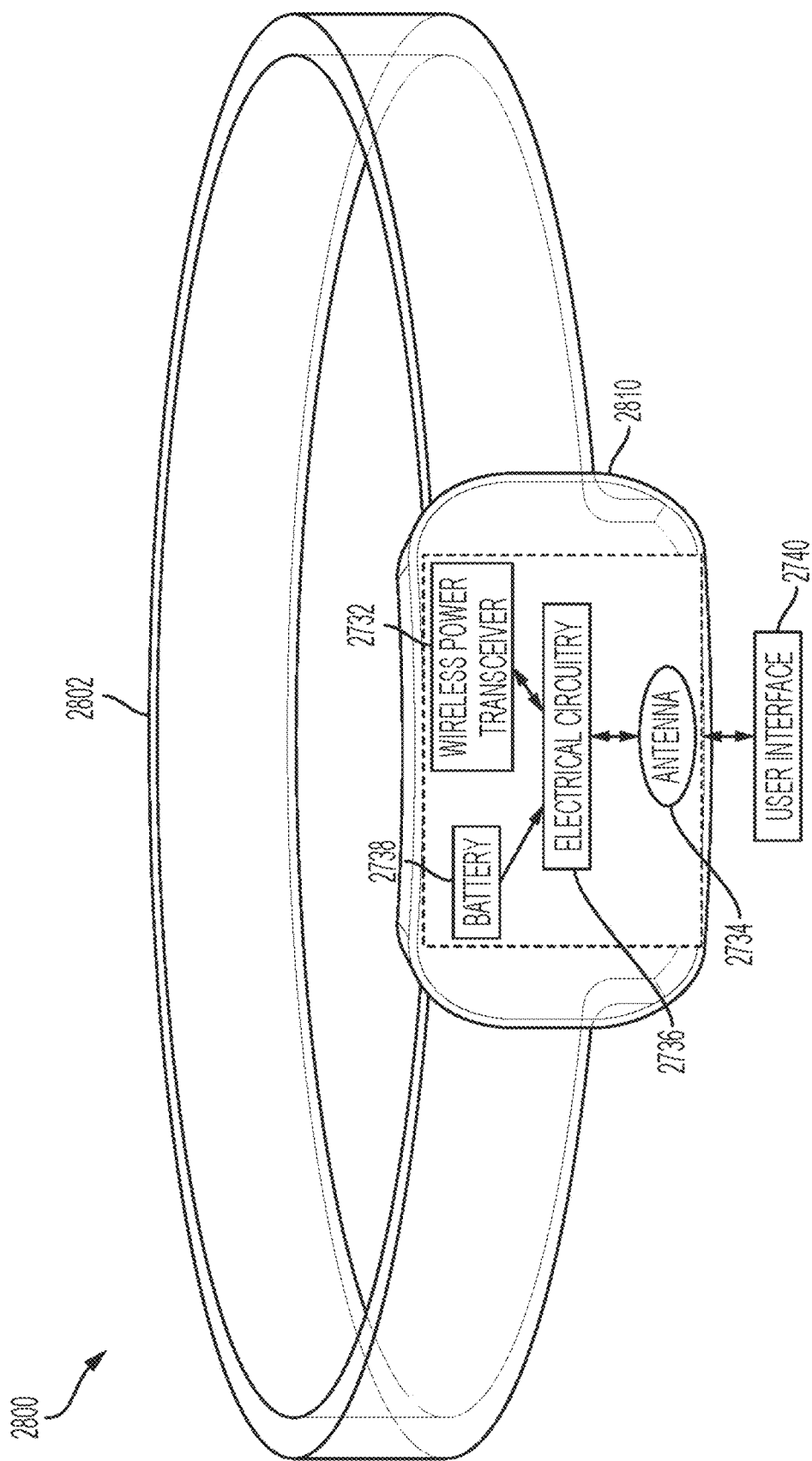
FIG. 28 is a sketch of a charging belt for a pessary device of the present invention according to some embodiments of the disclosure.

The components of master device 2730 may be fitted into many different forms for convenient powering of the pessary device 2710. In one embodiment, the master device 2730 may be attached to a pelvic belt to be worn by a patient having the pessary device 2710. FIG. 28 shows a charging belt 2800 for a pessary device. An enclosure 2810 may include the master device 2730. The enclosure 2810 may be affixed to a belt loop 2802. The enclosure 2810 may be attached to the belt loop 2802 in a manner to substantially align the wireless power transmitter with at least one power transceiving structure of the pessary when inserted into the vagina. For example, the pelvic belt may be fit to position the enclosure 2810 in a manner that a path from the enclosure 2810 to the pessary device in the patient substantially avoids the amniotic fluid of the patient that may obscure wireless signals. The belt loop 2802 may be made of an elastic material, such as cloth, silicone, or hook-and-loop fasteners, that conforms to a pregnant abdomen of a patient to operate across a range of gestation times and patient sizes. The antenna within enclosure 2810 may be sized to provide adequate wireless transmission capabilities for the range of positions of the pessary device 2710. The alignment of the enclosure 2810 to the pessary device location by the belt loop 2802 facilitates more efficient transfer of power to the pessary device and/or reception of data from the pessary device. In one embodiment, the arrangement of the enclosure 2810 by the belt loop 2802 may align a wireless power transmitter with one of the power transceiving structures described in the embodiments herein. For example, an inductive coil structure in the enclosure 2810 may be maintained in a position such that an electromagnetic field is aligned to have a straight path from a center of a coil structure in the enclosure 2810 to a center of a coil structure of the pessary device. When the pessary device has multiple wireless power transceiving structures of different orientations, alignment with a wireless transmitter structure of the pessary device may be easier and facilitate more efficient power transfer. For example, multiple wireless transceiver structures around the pessary device may allow efficient power transfer and/or data communications regardless of the radial orientation of the pessary device in the patient.

Figure 29A:
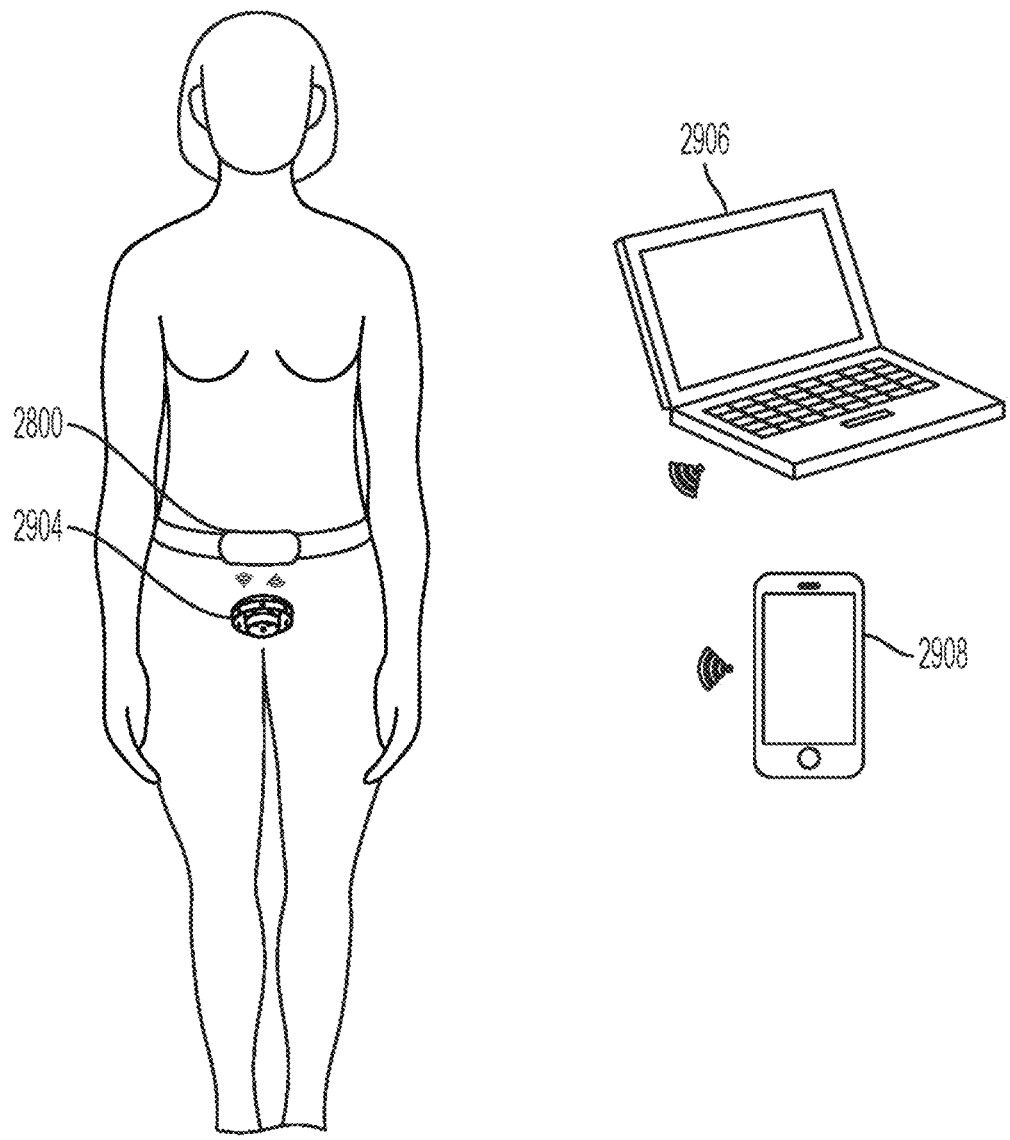
FIGS. 29A-B are sketches showing different views of a charging belt communicating with computing devices for interfacing with the pessary device of the present invention according to some embodiments of the disclosure.
Figure 29B:
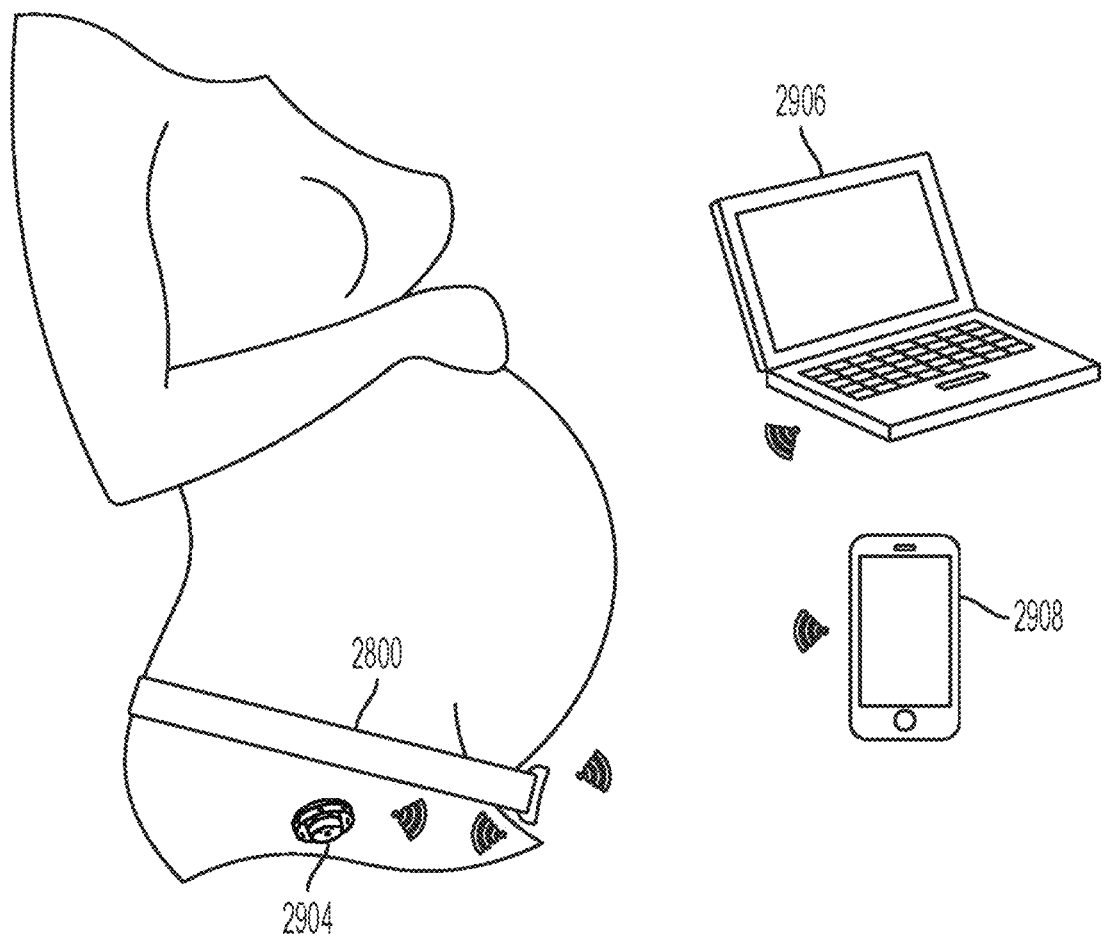

The wearing of the charging belt 2800 is shown in the sketches of FIGS. 29A-B. FIGS. 29A and 29B are front and lateral views, respectively, of a patient wearing a charging belt such as the example in FIG. 28. The charging belt 2800 may be positioned on the patient and oriented to provide wireless power to a pessary device 2904 inserted in the patient. The charging belt 2800 may relay data retrieved from the pessary device 2904 to computing devices 2906 and/or 2908, such as by allowing users of the devices 2906 and 2908 to access a user interface of the master device of the pelvic belt 2800.

Figure 30:
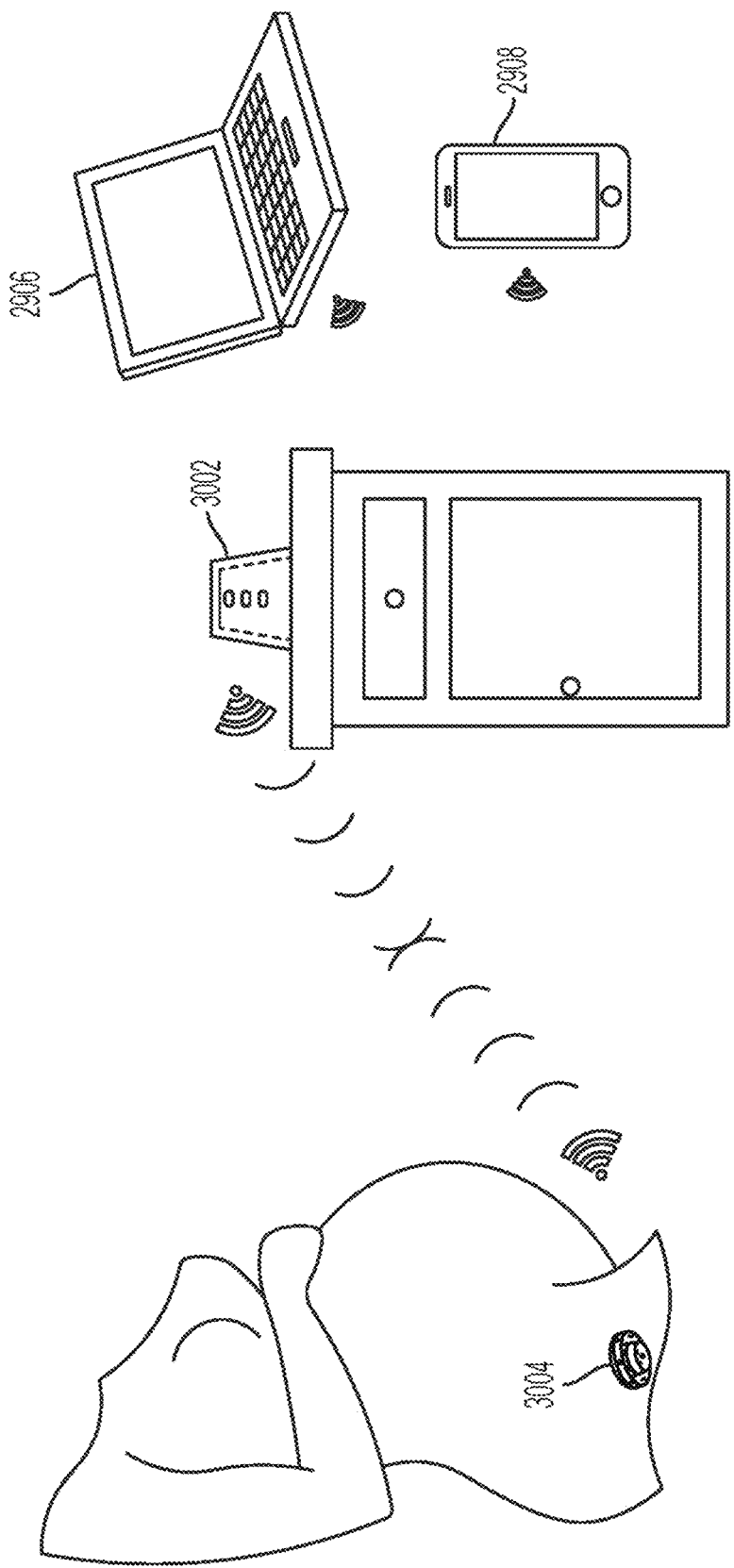
FIG. 30 is a sketch of a table-top charging device for a pessary device of the present invention according to some embodiments of the disclosure. with computing devices for interfacing with the pessary device of the present invention according to some embodiments of the disclosure.

In another embodiment, the master device 2730 may be integrated into a free-standing device, such as a table-top appliance 3002 shown in FIG. 30. The appliance 3002 may be plugged into a wall power source to provide power to a pessary device 3004 inserted in a patient. The appliance 3002 may include power transmitting structure capable of forming directional beams to target the power transfer to the pessary device in the patient as the patient moves. In one example, a signal strength of an identification signal transmitted in response to the wireless power RF signal may be used to estimate a location of the patient and track movement of the patient. In another example, motion data, such as from an accelerometer of the pessary, may be transmitted to the appliance 3002 to allow beam forming to track the patient's movement.

Figure 31:
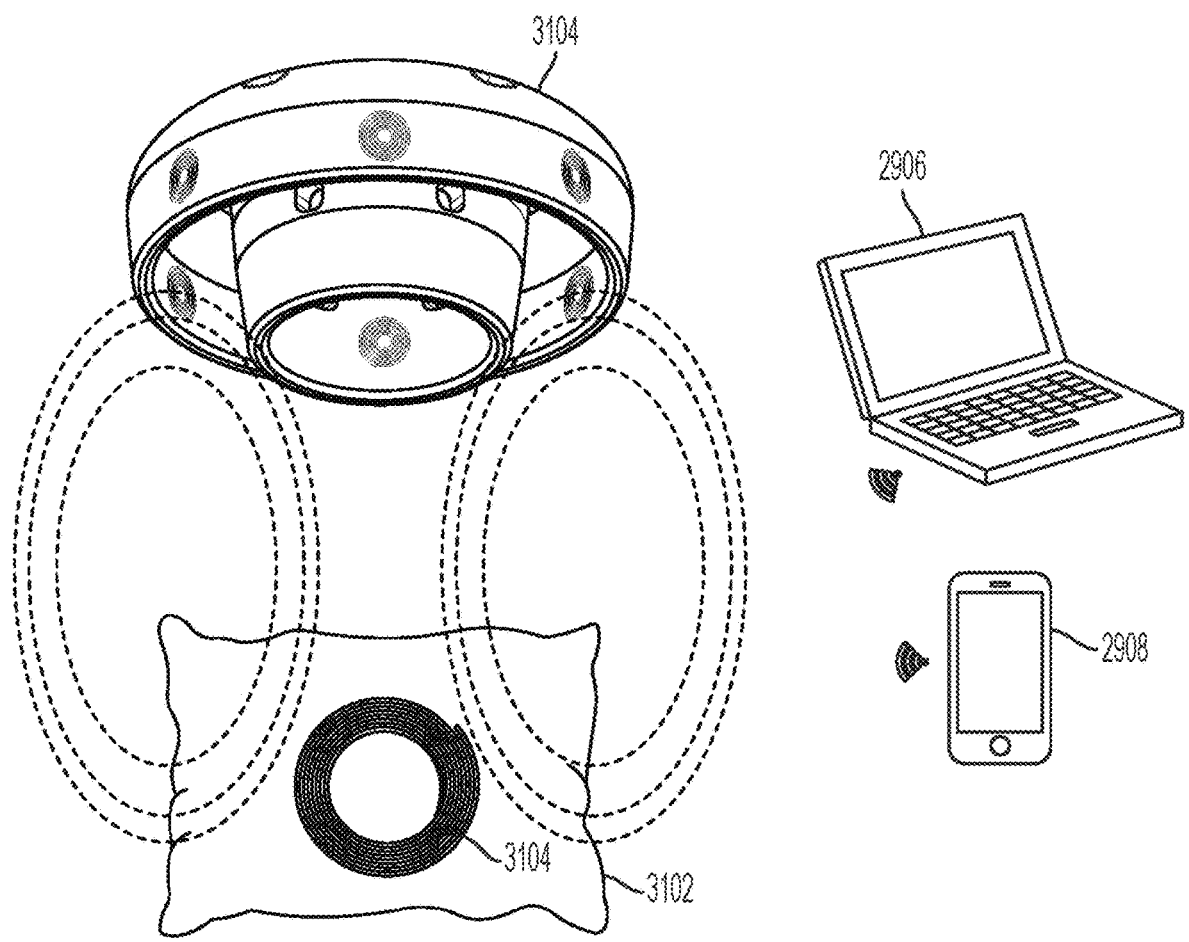
FIG. 31 is a sketch of a pillow charging device for a pessary device of the present invention according to some embodiments of the disclosure. with computing devices for interfacing with the pessary device of the present invention according to some embodiments of the disclosure.

In a further embodiment, the charger device 2730 may be integrated into a pillow 3102 shown in FIG. 31. The pillow 3102 may include filling, such as cotton or feathers, contained within an enclosure that is designed to provide supportive padding to a patient. An inductive coil 3104 for charging the pessary device 3104 may be included within the filling, such that the coil 3104 is generally unnoticeable to the patient. Additionally, a battery may be included within the filling to provide power for wirelessly powering the pessary device 3104. The pillow 3102 may be sized to fit between a patient's legs to place the pillow 3102 in position to provide wireless power to the pessary device 3104 when inserted in the patient while the patient sleeps. In some embodiments, the pillow may be between 20-50 centimeters by 15-50 centimeters.

Having thus described in detail a preferred selection of embodiments of the present invention, it is to be appreciated and will be apparent to those skilled in the art that many physical changes could be made in the apparatus without altering the inventive concepts and principles embodied therein. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

Preferred embodiments of the present disclosure thus offer advantages over the prior art and are well adapted to carry out one or more of the objects of this disclosure. However, the present invention does not require each of the components and acts described above. Any one or more of the above components, features and processes may be employed in any suitable configuration without inclusion of other such components, features and processes. Moreover, the present invention includes additional features, capabilities, functions, methods, uses and applications that have not been specifically addressed herein but are, or will become, apparent from the description herein, the appended drawings and claims.

The methods that may be described above or claimed herein and any other methods which may fall within the scope of the appended claims can be performed in any desired suitable order and are not necessarily limited to any sequence described herein or as may be listed in the appended claims. Further, the methods of the present invention do not necessarily require use of the particular embodiments shown and described herein, but are equally applicable with any other suitable structure, form and configuration of components.

While exemplary embodiments of the invention have been shown and described, many variations, modifications and/or changes of the system, apparatus and methods of the present invention, such as in the components, details of construction and operation, arrangement of parts and/or methods of use, are possible, contemplated by the patent applicant(s), within the scope of any appended claims, and may be made and used by one of ordinary skill in the art without departing from the spirit or teachings of the invention and scope of this disclosure and any appended claims. Thus, all matter herein set forth or shown in the accompanying drawings should be interpreted as illustrative, and the scope of the disclosure and any appended claims should not be limited to the embodiments described and shown herein.

What is claimed is:

1. An apparatus, comprising:
   a pessary, comprising:
     a first power transceiving structure attached to the pessary and configured to receive wireless power transmissions;
     electrical circuitry coupled to the first power transceiving structure, the electrical circuitry configured to monitor conditions in a vicinity of the pessary indicative of a preterm birth of a fetus, and the electrical circuitry configured to receive power from the wireless power transmissions received by the first power transceiving structure; and
     a ring, wherein upon final placement of the pessary within a vagina of a patient at least a portion of the ring is configured to contact at least a portion of the vagina,
   wherein the ring comprises a first edge and a second edge and an outer surface between said first and second edges and an interior surface between said first and second edges, and
   wherein the pessary further comprises:
     a sleeve having a first edge and a second edge and an outer surface between said first and second edges of said sleeve and an interior surface between said first and second edges of said sleeve, said sleeve generally supported within said ring; and
     an annular member having an outer edge and an inner edge, said outer edge of said annular member attached to the first edge of said ring and the inner edge of the annular member attached to the first edge of the sleeve supporting said sleeve within said ring, said annular member having a superior surface between the outer edge and inner edge of the annular member and an inferior surface opposite said superior surface,
   wherein upon final placement of the pessary within the vagina at least a portion of the interior surface of said sleeve being configured to contact at least a portion of the cervix and at least a portion of the superior surface of the annular member and at least a portion of the outer surface of the ring being configured to contact at least a portion of the vagina, and
   wherein the first power transceiving structure extends circumferentially between the first edge and the second edge of the ring around and spaced from the sleeve.

2. The apparatus of claim 1, wherein the first power transceiving structure comprises a spiral of wire forming a plurality of concentric circles.

3. The apparatus of claim 2, wherein the pessary further comprising a plurality of additional power transceiving structures attached to the ring and oriented facing different directions, coupled to the electrical circuitry, and configured to receive wireless power transmissions.

4. The apparatus of claim 1, wherein the electrical circuitry comprises a sensor configured to operate from the wireless power transmissions, and wherein the sensor is supported on the sleeve.

5. The apparatus of claim 4, wherein the sensor is configured to at least one of:
   generate an electrical current for delivery to the uterus to interrupt premature contractions of the uterus; or
   generate a signal based on at least one of: a pH of the patient proximate the cervix of the patient, a temperature of the patient proximate the cervix, a movement of the cervix, an orientation of the patient, a presence of contractions of the uterus, or premature uterine contractions.

6. The apparatus of claim 1, wherein a second power transceiving structure comprises a coiled wire extending away from the pessary.

7. The apparatus of claim 1, wherein the ring, sleeve, and annular member are molded as a unitary piece from a biocompatible polymer, and wherein the first power transceiving structure is configured to facilitate folding of the pessary for insertion into the vagina.

8. The apparatus of claim 1, wherein at least a portion of the pessary is coated with a biological beneficial medication.

9. An apparatus, comprising:
a pessary, comprising:
a first power transceiving structure attached to the pessary and configured to receive wireless power transmissions;
electrical circuitry coupled to the first power transceiving structure, the electrical circuitry configured to monitor conditions in a vicinity of the pessary indicative of a preterm birth of a fetus, and the electrical circuitry configured to receive power from the wireless power transmissions received by the first power transceiving structure,
wherein:
the first power transceiving structure comprises a radial pattern extending around a circumference of a first portion of the pessary, wherein the radial pattern repeats multiple times around the circumference of the first portion of the pessary;
the first portion of the pessary comprises a ring;
a second portion of the pessary comprises a sleeve;
the ring comprises a first edge and a second edge and an outer surface between said first and second edges and an interior surface between said first and second edges; and
the sleeve comprises a first edge and a second edge and an outer surface between said first and second edges of said sleeve and an interior surface between said first and second edges of said sleeve, the sleeve generally supported within the ring, and
the pessary further comprising:
an annular member having an outer edge and an inner edge, said outer edge of said annular member attached to the first edge of said ring and the inner edge of the annular member attached to the first edge of the sleeve supporting said sleeve within said ring, said annular member having a superior surface between the outer edge and inner edge of the annular member and an inferior surface opposite said superior surface,
wherein upon final placement of the pessary within the vagina at least a portion of the interior surface of said sleeve being configured to contact at least a portion of the cervix and at least a portion of the superior surface of the annular member and at least a portion of the outer surface of the ring being configured to contact at least a portion of the vagina, and
wherein the first power transceiving structure extends circumferentially between the first edge and the second edge of the ring around and spaced from the sleeve.

10. The apparatus of claim 9, wherein the radial pattern of the first power transceiving structure comprises a plurality of turns, each turn changing the first power transceiving structure from oriented towards a first side of the pessary to oriented towards a second side of the pessary, wherein the plurality of turns in the radial pattern facilitate at least one of folding or collapsing of the pessary for insertion into the vagina.

11. The apparatus of claim 9, wherein the pessary further comprises a second power transceiving structure configured to receive wireless power transmissions, wherein the second power transceiving structure comprises a radial pattern extending around a second circumference of the second portion of the pessary.

12. The apparatus of claim 9, wherein said ring, sleeve, and annular member are pliable, and wherein the first power transceiving structure is configured to facilitate folding of the pessary for insertion into the vagina.

* * * * *